(12) United States Patent
Moore et al.

(10) Patent No.: US 7,927,800 B2
(45) Date of Patent: Apr. 19, 2011

(54) ASSOCIATIONS OF POLYMORPHISMS IN THE FIBROBLAST GROWTH FACTOR 8 (FGF8) AND ITS HAPLOTYPES WITH CARCASS QUALITY, GROWTH AND FEED EFFICIENCY IN BEEF CATTLE

(75) Inventors: Stephen Stewart Moore, Edmonton (CA); Elisa Ferreira Marques, Edmonton (CA)

(73) Assignee: University of Alberta (CA)

( * ) Notice: Subject to any disclaimer, the term of this patent is extended or adjusted under 35 U.S.C. 154(b) by 487 days.

(21) Appl. No.: 11/969,788

(22) Filed: Jan. 4, 2008

(65) Prior Publication Data

US 2009/0043599 A1 Feb. 12, 2009

Related U.S. Application Data

(60) Provisional application No. 60/878,721, filed on Jan. 4, 2007.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

2005/0202484 A1  9/2005  Moore et al.

FOREIGN PATENT DOCUMENTS
WO     WO 2005/104775 A2    11/2005

OTHER PUBLICATIONS

Juppner H. Bone (Aug. 1995) vol. 17, No. 2, Supplment pp. 39S-42S.*
Hacker U.T. et al. Gut (May 1997), vol. 40, No. 5, pp. 623-627.*
Marques et al. Abstract from Plant & Animal Genomes XV Conference. Abstract identified as W69: Cattle/Sheep, accessed from: http://www.intl-pag.org/15/abstracts/PAG15_W10_69.html on Jun. 16, 2010.*
Draft program of Plant and Animal Genome XV Program. accessed from: http://www.intl-pag.org/15/15-pag.html, on Jun. 16, 2010, twelve pages.*
Kenney-Hunt et al., Quantitative trait loci for body size components in mice, Mammalian Genome, Jun. 2006, vol. 17, No. 6, pp. 526-537.
FGF8—SNP Results, ENTREZ SNP (online). (Retrieved on Jul. 25, 2008). Retrieved from the internet: <URL: http://www.ncbi.nlm.nih.gov/sites/entrez.

* cited by examiner

*Primary Examiner* — Juliet C Switzer
(74) *Attorney, Agent, or Firm* — Judy Jarecki-Black; Chad Kitchen; Merial Limited

(57) ABSTRACT

The physiological regulation of intake, growth and energy partitioning in animals is under the control of multiple genes, which may be important candidates for unraveling the genetic variation in economically relevant traits in beef production. The present invention relates to the identification of single nucleotide polymorphisms (SNPs) within the bovine gene encoding fibroblast growth factor 8 ("FGF8") and their associations with economically relevant traits in beef production. The invention further encompasses methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

3 Claims, 13 Drawing Sheets

```
LOCUS       NW_930497               9790 bp    DNA     linear   CON 30-SEP-2005
DEFINITION  Bos taurus chromosome 26 genomic contig, whole genome shotgun
            sequence.
ACCESSION   NW_930497 REGION: complement(134721..144510)
VERSION     NW_930497.1  GI:76654960
KEYWORDS    WGS.
SOURCE      Bos taurus (cattle)
  ORGANISM  Bos taurus
            Eukaryota; Metazoa; Chordata; Craniata; Vertebrata;
            Euteleostomi; Mammalia; Eutheria; Laurasiatheria;
            Cetartiodactyla; Ruminantia; Pecora; Bovidae; Bovinae; Bos.
REFERENCE   1  (sites)
  AUTHORS   Lowe,T.M. and Eddy,S.R.
  TITLE     tRNAscan-SE: a program for improved detection of transfer RNA
            genes in genomic sequence
  JOURNAL   Nucleic Acids Res. 25 (5), 955-964 (1997)
   PUBMED   9023104
  REMARK    This is the methods paper for tRNAscan-SE.

COMMENT     GENOME ANNOTATION REFSEQ:  Features on this sequence have been
            produced for build 2 version 1 of the NCBI's genome annotation
            [see documentation].The DNA sequence is from the whole genome
            assembly released by the Baylor College of Medicine Human
            Genome Sequencing Center as Btau_2.0, 29 June 2005(see
ORIGIN
[SEQ ID NO 1]
    1 atgtgcatcc ctggccccat gaaggggct caggccccaa gaggacctgt gaggggtaag
   61 gtagaggcca atctttgctc ctcctaccag tcatgcaggc catctctgag ccagcctgga
  121 cccttagaaa cctgattcca ggggccagat ggaggggct ggccagattg ggtgacaggg
  181 aaaccagaat ccgggtggcc tggcatatgg gggcagagag gagcccctgg gattcagcct
  241 cctgggctaa agggttccag cccctagcc ctccacctgg tctggggatg ggggcggac
  301 cgttctctgg tgcctgaaat caggtggttc tggggattgg ctgctgctgt accaggaaga
  361 gaaagggatg tacctagtgt gagcatgagt gtgtatatga ccaagtctga ggtcagtagt
  421 tcagcagctg tgttgatggg gcaggggtc tcagtgccct acaaacaaac aaacaaaagg
  481 ttacctcctg agacagcctg gggccagaca tgctgaggag ggacacagaa gagtgcctgg
  541 tggggccagg cccactccct cccacattgg cttctgggca aatgagtgaa caagtgggag
  601 gggtccctgg ataaccagaa gaggttggca ttggagcagg tgtttggaaa gagtgtttcc
  661 acaacacaga aaagcactcc cttttcaaca catctccgaa ggaggtgccc ttctccctat
  721 ggtgaggagc aaacaggtcc agggtttaac ctccccttt cctagttgag gataaaggaa
  781 gatgatccct ctctgcgtcg cagtgatcag ggtcgcaggc ctctctcttt gctgcaggac
  841 tttcctgaag tgcttccacc aagaacactg ggatggagag ggcagccagg atgggaccat
  901 tcaccaaccg caggcaaggg gtcaggagac agaggagaag gtggagttgg cgccctctgg
  961 tgggcgaggt tgaaaccgct tgtggctgtg cagcttccca cgccgcctct gtagcggctc
 1021 aaggccggcg ccgcggtgca ggggcctaca tgtcccgcca gccgtctgcg cgactaaggc
 1081 agacttcatt cgttggttcg ttcattcatt cactggaagg gttcctgtta gaacccttcc
 1141 cttcctcctc tcgtctatcg cctccaaagt cctcggcacg tgttcggttg aaggcacggt
 1201 agtctggctg agtgtaggga aaagttgggg aatccttccc agccgacact tctacccccc
 1261 gcaagtagcc ccgcccaat atttaccctc ctcgacgccg ctgatcgctc attgtgagcc
 1321 cttctagttt cttggcgggt ctgccgcgg ccctggccgg cgccaagcgc gctcctaccc
 1381 gcggtggggg cccaatccac atccgcctcg tcccggagtt tctcgacccg acagggcgcc
 1441 cacggactga gccgggaatt gttttttctc cctccctcc ctcgtctctc ctcgatcccc
 1501 ctttctgccc tctcagcgca cagtaggagc gttgcccatt catttcggtc tctgagccct
 1561 gagggcttac gccgcggttt gcagactgct ggaggagggg caagactgta tttgggggtc
 1621 gaaggggac gaccagacgg ggcctagagt gcttaacaca gtctctgcga tttacatttg
 1681 aacagtcggc ggagggtctg cggcgctttg aacgcctggt gcaggctgcg cgtgttggag
 1741 cgcaggcggc ccccgccggt tggtgtggat ttgaggggcc cagggtgggc caggggcggt
 1801 gggagtgggc gaccgatgcg tttggaaaga ggctgagcgt gtgtgtttgg gcccttgcaa
 1861 cggtgtattt gcagagaggg gctatttgtg ttggcgagag gtgtgtgttt gtgtttgcag
```

FIG. 1

```
1921 gaggcgagtg actctgtgtg tgtgtatttg tgtttgagga gtgtggggac ggccgggaaa
1981 ggtggccggg ctgtcactca gcgatcaggt tgacaggcgc tccctcatca gggccaggga
2041 gctctgattg cagattcgag gaaacaaaat agcaattgta attacgggc tttgataaga
2101 taaaggaagg agcaagccgg ccgggaggcg agtaagagca agggaggaga gaacggcctg
2161 ctggggcccc gatggagtat tcacatctgt cNNNNNNNNN NNNNNNNNNN NNNNNNNNNN
2221 NNNNNNNNNN NNNNNNNNNN Ncaccccctc ccccatctag ggacaggggac ttttggggat
2281 atgagaagaa tctcctcaaa tggacgaaga cccagttggg ggaagttctc aaaatgtaga
2341 ggaattctgg tctgtatagg ccccggggt agaggttagg gtgtgggact caaaccctga
2401 ttgatggtcc acacgtttag gccggggatg gcccatctct cggggagagt gaagagggtg
2461 gattaagatc attgaggttc agcccagcat cttcagaacc ttttgggggc tccaaaccag
2521 ggttgaactc tggtctgagc caggtgctat agtctccacc ccccactctg ggaaaaggca
2581 ggtgcccaga gtgactcagg ttgtgactcc aggactacac acgctaagga tgggctggat
2641 gatgccctga cccctgcttg ggtcctgctt cttgctgttc tcatcagact gttttcagag
2701 ggctggtccc tggtgagaag accccttttca tctgctgcct ctcatctctc cacttattta
2761 ttaatgcata caaataataa acatattcaa gggcctccta tgtgcagggc atgaggttaa
2821 gatggtgaat atttgcctg cttgaattag tgtacctggg gatgtagaca cccaacaact
2881 tctaagacag aggagctcaa atgaaggaga aatgctggtc taggcagtgg gtactggagc
2941 ccacttcact tgtcttcccc cagtgcccac ctcccagtgg ggttgagagg agatggtgca
3001 gacagccttt agcaaataca agtgctcaat aaatggtggt gcttatgatt cttatctgtt
3061 gggagggtgg tgaaggcaag gccccgcctg cactgaggtc taaatgctca gtcagtttcc
3121 ccattattca ttcattaaat acagaattgc agaaccctgc cctgctctcc tgagctagta
3181 agatgtggtc cttgcctgga ggtctgggtg ggaaagagcc acttgaggga acagactcaa
3241 gtgggtaaca ggtgagctca gggagtctgc ttctctgggg agggatgaga tcttgggaca
3301 agtctcctga ttctgtttcc ccatctagac cttgctcagt attagcacta tggctgggag
3361 tgggaaaggc aggccacaga gaaagggaa gaacttggct gtgctgcctc tggtctcttg
3421 gttcctgag gccatcccag cccctccagc ccaatcccca aggacatggg ggctggcagt
3481 agggcagggg aggtcttggg caagggcagc agctgggcaa agcatcagtg gctccacctg
3541 ctccccagaa ttttctgtct cagggcatct ctgcccaccc aagctgctct caaagaagca
3601 ccacacctcg cgggttcctg aagcccctgg aggaagcaat gggcggctgg gaaaggctta
3661 gacaactcac taccttcttt gatactttcc cctcccccag ggttgacaaa tcaccagtcc
3721 aagtttacca cacagtaggt gtgtaagtac ctgttcattg cacaaatagt gggactctga
3781 gcgaaaaaga ctaggcaacc tggatctaag tctctttccc aggaaaagca gctgaggtta
3841 ttttgcgccc actgctgct gctttgggga gagcatggtg gtggcagtga ctgggttttt
3901 ccgtatgggt gggctctctc cttttgggt ggtgtggtca ggcttcagtc tagcgtgttg
3961 ggggcgggag gtcgggggc ggacaggagc agggtgatg gtgataatga gagcaggaag
4021 caggaaagga gatgttcctc gatctcaggg ccttcttggt gactgaacga tgcaggagag
4081 accggcaagg cagggtactc agcaggaaga tgggagtggt tgtcggctcc cggtcgcaca
4141 ggcacgcact gccagaggaa agcgcacaac cgttcacccc agagttagag gctacttgca
4201 ggcggcagcc ccagacagac aaagcacaca gtaggtggct cagagaaccg ctgtctagct
4261 tgaggcttaa gcggaccggg tccacggtg gagaccgggc gccttccac tcgggcgccc
4321 gggggggtcca ggaagcccca gcagagggtc tcgggactcc acgggtggg cgcccgatg
4381 ggcccccatc cccgcgtgcc tggaccccaa gaacgcgcaa gggacaagt ccgggatgcg
4441 gagaggcgNN NNNNNNNNNN NNNNNNNNNN NNNNNNNNNN NNNNNNNNNN NNNNNNNNNN
4501 NNNNNNNNNN NNNNNNNNNN NNNNNNNNNN NNNNNNNNNN NNNNNNNNNN NNNNNNNNNN
4561 NNNNNNNNNN NNNNNNNNNN NNNNNNNNNN NNNNNNNNNN NNNNNNNNNN NNNNNNNNNN
4621 NNNNNNNNNN NNNNNcagcc aggtggggt ggttggggaa ctcggcgggc agccactccc
4681 ggccgcgccg aggaaggggg cattcggagc caggggcat tcgatgtcag aggtccggtg
4741 actgcctcag ggacccgctc cgcggctctt tggggagact tggcggcggg tctggccgaa
4801 agatcaggtg cccgggtctt ctgtggtctc aacatttgct ccgtgaattt gtctttataa
4861 atgtcagggg tcgggccgct ctgcctcccg acttaaaagc gccctgctct tctaggaagg
4921 cccgggcggg gggcctgcgt tgggcaggga gctcgcttcc ctgttccgag ctggccggga
4981 gtcccagggt gtttcccaac aggtgggtcc agatcctccc ccatcccggg cgcatccata
5041 ctagactggg tctgtccgac ttccttgggt agggtggggg tggtccgaac tggcatgttg
5101 gggggaccc agccctgcc ggctgcctgg gcagtggag ggaggtgccg ggtgatgggg
5161 gccactcggg ccctgggca gggtagcatt ataatggcgt gttgtgtatt tttcaatttc
5221 ctaaaggtaa ctgttcagtc ctcacctaat tttacacagc atgtgaggga gcagagcctg
5281 gtgacagatc agctcagccg ccgtctcatc cggacctacc aactctacag ccgcaccagc
5341 gggaagcacg tgcaggttct ggccaacaag cgcatcaacg ccatggcaga agacgggggac
```

FIG. 1 (Continued)

```
5401 cccttcggta aggagctaca ctgcactggg gttaaggtag tctgcggggc gcgcccctcc
5461 tccccaggct ggcctgctgt gacgggaccc agcagtcgcg tctgcgctga gctgaggcct
5521 gcaggctccc cagctcagaa gggaaggagt taagccgaca aagcatcttg ggggtcagct
5581 ggagaagaga gggctgggga agggaccctg gggagtactt ggcccatagg tgccctttcc
5641 ctgcccagca gatgaatgaa gccaggaatc tccctttcca cctcccccctc tcataccct
5701 ccccactgca ggtggaggca gagggttcag ggggagggg cccaggttta agggaagctc
5761 ttgaaagagg atatgtcacc agggcccaca aaagcagagt gggaaagaga agggagagaa
5821 atccctcaa ctctcccagg tttgggggc ggtgtactgc gaactttaaa tactttgatc
5881 aggagggtca attacacatg gggactaggc taggaaaggg gccttcccca cttcacttgt
5941 ccaggaaccc aggcggttgg tcagagcggg gctcctggct cccggtgggg tggtgagtac
6001 agggagctac tgtgggatgg agaggctgag gactgattga tttctaaaac attcaatatt
6061 cctgccttga aacaaggcca atttccagag tcctggatgt accaagagaa aagcaagtcc
6121 tctgggcggc tggtgttgtt tttagagagc gattattgtg agtttaaaaa cctttaaata
6181 atgaccaagt taaacaagca tgaaggaga ggggaagact ctattaaaat gtaataaaaa
6241 ggtgaagcat tttaagagct aagaagaaaa atgaagaatg atataaaaca gaaaagaac
6301 gagccttttt ttcagatgtg gagtttgaaa ggagttgcaa gtctgtaaat gttaaaaaag
6361 aggttcaaga ttgttctcta tgaatctctg gagagacccc cgcgtctggc agagcgatta
6421 aaactcttct tactttcacc tttttttaaca tttcctgaat actttctcct cttctcgagc
6481 cagtttgggg gatcgagtat gtctcgctgc atttttctg catcgacgta gctgacttcc
6541 cttcaaagct ggagaaggag acataatttt cctgggataa atctgtcact ggggtggaag
6601 aataggtttg aaaatgttaa gctttccaaa agcccggtcg ggaaagccgc tgtaaactgc
6661 cgccccagct cccagctcc atccaggaag gagagtgggg gctttctgca gtgggggtgg
6721 gggtggcctg cccggtggcc gagctcccct gctgggctgg caggggccagc ctgccgcccc
6781 tttgtcccctt caaactggct gctcgttgcc cttctcagct tccaaggaaa gggaatgaat
6841 gcctggctcc tcctgggttt gctccattgg agcaaatggt ccagcatcct ccgggtttgg
6901 ggagcgaaga agacgctaag ctggtcatgg gggattcat cttcagacat cagaagtctg
6961 atgcccactt ctcttcttac aattatatga ggcttcccag gttccctggt ccctgcctgg
7021 tggcaggag caggagctgg agggcccaag agcagaggct tagggtgtat agccaggaca
7081 ggtagaatct ggggagaatg gcaaaNNNNN NNNNNNNNNN NNNNNNNNNN NNNNNNNNNN
7141 NNNNNNNNNN NNNNNNNNNN NNNNNNNNNN NNNNNNNNNN NNNNNNNNNN NNNNNNNNNN
7201 NNNNNNNNNN NNNNNNNNNN NNNNNNNNNN NNNNNNNNNN NNNNNNNNNN NNNNNNNNNN
7261 NNNNNNNNNN NNNNNNNNNN NNNNNNNNNN NNNNNNNNNN NNNNNNNNNN NNNNNNNNNN
7321 NNtctatgct tctgcaaagg gaggcaggca gtcacaggct gggctgtgag ggctgccttg
7381 ctgacctgtg cccatcacct cccattagtt tcagggtcag agaaggtgcc accttgtcag
7441 aataagctgg gaggtagccc tgggagtcac cagacttctt tgtcaaggag ggagaaggct
7501 gaaggaggga gggcaggaga cccagcccct ttggttccat cccaaacagc taagtcggtc
7561 ctcactctca aagggaggag ttgtacagag agtgggcagg gccagggct tctgtggcaa
7621 gctggctgtc taaggaagg ggtaagaagg cacaggattc agctccctgt ctcctggctc
7681 ttgagtgaga ggcaagcaca catgatttc tcttctcctc ccctacagaa agtgtttgct
7741 cactggggta agaagcccag tgctgctaga gggggtgcaa gagaaaagac tattgaatta
7801 ctgacttctg aacactgggg ctggggtctg gagtgactgg gaagtatggg gaagagacag
7861 tatcctccta gctggtgtct gagtttctag gaaagcagcc agccatgggc tgtgtgtgga
7921 gggagagctg tcctcatccc tgtcaccttt gcagcagagc cggggtggag ggtggaagat
7981 gtggggtggg gtggagtggg ttggggtgga gggtgtcggg gggtggccaa ggctgtgggt
8041 tggaacccga ggtatcagaa gcaagagaga gtgcttttat gtttgacctc aggagtggag
8101 gtcaccactg cacctggatg tttgtaataa cctgtgaggc acgtgcatat aatattttga
8161 actggaagaa tcctcataga tcttttgatt ggtagtggaa ttctagtcaa attaaatttt
8221 acttgaagcc tcaacacaaa aatcattgct gtctgattat aaaaagggt cttcagtttg
8281 atggctctaa gacccctctg cataaaccag ttcagacacc atgatctcat ccattcccc
8341 tctgtaaacc caggctaggg gcctgaagcc cagaaagggg acttgacctt tccaggggttg
8401 cacagcatat tagtggttgg agcccacagc ctgggcatct ggcccttgga gcagctgctt
8461 ctgggatggg ccagctgggg tagggacatg gagcactgga ggtcaggaag ctgccaataa
8521 ccaccccac cccacccaa ccttttcctga cagcaaagct catcgtggag acagacacct
8581 tcggagccg ggttcgagta cgaggagctg agacaggcct ctacatctgc atgaacaaga
8641 agggaaaatt gattgccaag gtgaggtcct agaaagaagg gagggactgg ctagggcctg
8701 gggagcaggc tgggctggct gagctcctcc aggataccaa ctaagtgggc agagaggcag
```

FIG. 1 (Continued)

```
8761 agggccacct tggggttacc taatgattgg gtgggggtg gaggaggtga gggaggaggt
8821 aactgagaga tgaaaagcta taaaggcaaa ggaggaagaa ggaaggctag ggaaggggct
8881 ggggaggggg tgtcggtaaa ttccatatat cttttaaca aatcaccaaa ttgctttgct
8941 attatgtcca attacatggt accagcattt ggaatgttca gtaagccgag ggcccagccc
9001 ctcagccgag ctctgaaatg gccccattag tcacggctcc tctccagcct cgagctcccc
9061 gcttccctgg cttctggggc ccggggctca gcatctcctc accagccttc cctcccccat
9121 agggtggtgg ccctggggct gcaggttagc gtcctgagat ggctgaggtg ggcaggtggg
9181 gaaacgggtg ctagcagctt gggccagact ggtgggcagg aggccagggt gggcaggggc
9241 tgggccccct ctctgcccct ctgtgttggg gcccagcccc tctgtagaca gccatgtgtc
9301 actgctaccc aggaggacag gaagttgccg ggtgggctgt gagttgtgag ggattagaga
9361 gcgggtgccc accctgccat ctgctgggt gcccacctgc tgtctggggc cgcctgccct
9421 ctgcctagga tgggaggggg ctccggacag agccgggtga caccgtgtct gccccccacc
9481 ctgcagagca acggcaaagg caaggactgc gtgttcacgg agatcgtgct ggagaacaat
9541 tacacggccc tgcagaacgc caagtacgag ggctggtaca tggctttcac gcgcaaaggc
9601 cgaccccgca agggctccaa gacccggcag caccagcgcg aagtccactt catgaagcgg
9661 ctgccccgcg gccaccacac caccgagcag agcctgcgct tcgagttcct caactacccg
9721 cccttcacgc gcagcctgcg cggcagccag aggacttggg cccctgagcc ccgataggcc
9781 ctgccggccc
```

FIG. 1 (Continued)

2199-05_FGF8 (SNP14-SNP15) - REVERSE SEQUENCE
[SEQ ID NO 2]
GCGCACAGTAGGAGCGTTGCCCATTCATTTCGGTCTCTGAGCCCTGAGGGCTTACGCCGCG
GTTTGCAGACTGCTGGAGGAGGGGCAAGACTGTATTTGGGGG[T/G]CGAAGGGGGACGAC
CAGACGGGGCCTA[G/A]AGTGCTTAACACAGTCTCTGCGATTTACATTTGAACAGTCGGC
GGAGGGTCTGCGGCGCTTTGAACGCCTGGTGCAGGCTGCGCGTGTTGGAGCGCAGGCGGCC
CCCGCCGGTTGGTGTGGATTTGAGGGGCCCAGGGTGGGCCAGGGGCGGTGGGAGTGGGCGA
CCGATGCGTTTGGAAAGAGGCTGAGCGTGTGTGTTTGGGCCCTTGCAACGGTGTATTTGCA
GAGAGGGGCTATTTGTGTTGGCGAGAGGTGTGTGTTTGTGTTTGCAGGAGGCGAGTGACTC
TGTGTGTGTGTATTTGTGTTTGAGGAGTGTGGGGACGGCCGGGAAAGGTGGCCGGGCTGTC
ACTCAGCG

FIG. 2A

FGF8 –SNP14 – FORWARD SEQUENCE
[SEQ ID NO 3]
CAAAGCGCCGCAGACCCTCCGCCGACTGTTCAAATGTAAATCGCAGAGACTGTGTTAAGCA
CTCTAGGCCCCGTCTGGTCGTCCCCCTTCG[C/A]CCCCAAATACAGTCTTGCCCCTCCT
CCAGCAGTCTGCAAACCGCGGCGTAAGCCCTCAGGGCTCAGAGACCGAAATGAATGGGCAA
C

FIG. 2B

FGF8 – SNP15 - FORWARD SEQUENCE
[SEQ ID NO 4]
CAAAGCGCCGCAGACCCTCCGCCGACTGTTCAAATGTAAATCGCAGAGACTGTGTTAAGCA
CT[C/T]TAGGCCCCGTCTGGTCGTCCCCCTTCGACCCCAAATACAGTCTTGCCCCTCCT
CCAGCAGTCTGCAAACCGCGGCGTAAGCCCTCAGGGCTCAGAGACCGAAATGAATGGGCAA
C

FIG. 2C

193-05_FGF8 (SNP16) - REVERSE SEQUENCE
[SEQ ID NO 5]
CGATCCCCTTTCTGCCCTCTCAGCGCACAGTAGGAGCGTTGCCCATTCATTTCGGTCTCTG
AGCCCTGAGGGCTTACGCCGCGGTTTGCAGACTGCTGGAGGAGGGGCAAGACTGTATTTGG
GGGGCGAAGGGGGACGACCAGACGGGGCCTAAAGTGCTTAACACAGTCTCTGCGATTTACA
TTTGAACAGTCGGCGGAGGGTCTGCGGCGCTTTGAACGCCTGGTGCAGGCTGCGCGTGTTG
GAGCGCAGGCGGCCCCCGCCGGTTGGTGTGGATTTGAGGGGCCCAGGGTGGGCCAGGGGCG
GTGGGAGTGGGCGACCGATGCGTTTGGAAAGAGGCTGAGCGTGTGTGTTTGGGCCCTTGCA
ACGGTGTATTTGCAGAGAGGGCTATTTGTGTTGGCGAGAGGTGT[G/C]TGTTTGTGTTT
GCAGGAGGCGAGTGACTCTGTGTGTGTGTATTTGTGTTGGAGGAGTGTGGGGACGGCCGGG
AAAGGTGGCCGGGCTGTCACTCAGCGATCGGGGTTGGACAGA

FIG. 3A

FGF8 – SNP 16 – FORWARD SEQUENCE
[SEQ ID NO 6]
CAAATACACACACACAGAGTCACTCGCCTCCTGCAAACACAAACACACACCTCTCGCCAAC
AAATACACACACACAGAGTCACTCGCCTCCTGCAAACACAAACA[C/G]ACACCTCTCGCC
AACACAAATAGCCCCTCTCTGCAAATACACCGTTGCAAGGGCCCAAACACACACGCTCAGC
C

FIG. 3B

341-03_FGF8 (SNP17) - REVERSE SEQUENCE
[SEQ ID NO 7]
CTGCTCGCGGCTCTTTGGGGAGACTTGGCGGCGGGTCTGGCCGAAAGATCAGGTGCCCGGG
TCTTCTGT[G/C]GTCTCAACATTTGCTCCGTGAATTTGTCTTTATAAATGTCAGGGGTCG
GGCCGCTCTGCCTCCCGACTTAAAAGCGCCCTGCTCTTCTAGGAAGGCCCGGGCGGGGGGC
CTGCGTTGGGCAGGGAGCTCGCTTCCCTGTTCCGAGCTGGCCGGGAGTCCCAGGGTGTTTC
CCAACAGGTGGGTCCAGATCCTTCCCCATCCCGGGCGCATCCATACTAGACTGGGTCTGTC
CGACTTCCTTGGGTAGGGTGGATGAGTCCTATTTTAGTTTATAAAGCTCCTTTTTTTTTAT
AGGTTTCTAGCCGGTTTTTTTTTATTTTTTATTTGTTTATTTTTTTTTTTTCTTTTTTT
GTTTTTTTTTTTTTTTTTTTTTGTTTTTTTTTTTTTTTATTT

FIG. 4A

FGF8 – SNP 17 – FORWARD SEQUENCE
[SEQ ID NO 8]
CGGGAGGCAGAGCGGCCCGACCCCTGACATTTATAAAGACAAATTCACGGAGCAAATGTTG
AGAC[C/G]ACAGAAGACCCGGGCACCTGATCTTTCGGCCAGACCCGCCGCCAAGTCTCCC
CAAAGAGCCGCGGAGCGGGTCCCTGAGGCAGTCACCGGACCTCTGACATCGAATGCCCCCT
G

FIG. 4B

ASSOCIATIONS OF POLYMORPHISMS IN THE FIBROBLAST GROWTH FACTOR 8 (FGF8) AND ITS HAPLOTYPES WITH CARCASS QUALITY, GROWTH AND FEED EFFICIENCY IN BEEF CATTLE

INCORPORATION BY REFERENCE

This application claims benefit of U.S. provisional patent application Ser. No. 60/878,721 filed Jan. 4, 2007.

The foregoing applications, and all documents cited therein or during their prosecution ("appln cited documents") and all documents cited or referenced in the appln cited documents, and all documents cited or referenced herein ("herein cited documents"), together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the identification of single nucleotide polymorphisms (SNPs) within the bovine genes encoding fibroblast growth factor 8 ("FGF8") and their associations with economically relevant traits in beef production. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is resistance to the introduction and use of such methodologies. Such methodologies are also non-inheritable and need to be applied differently in every production system.

There is a need for methods that allow relatively easy and more efficient selection and breeding of farm animals with an advantage for an inheritable trait of circulating leptin levels, feed intake, growth rate, body weight, carcass merit and carcass composition. The economic significance of the use of genetic markers that are associated with specific economically important traits (especially traits with low heritability) in livestock through marker-assisted selection cannot therefore be over-emphasized.

The physiological regulation of intake, growth and energy partitioning in animals is under the control of multiple genes, which may be important candidates for unraveling the genetic variation in economically relevant traits (ERT) in beef production. Polymorphisms in these candidate genes that show association with specific ERT are useful quantitative trait nucleotides for marker-assisted selection.

The fibroblast growth factor (FGF) family consists of at least eighteen distinct secreted proteins (Basilico et al., Adv. Cancer Res. 59:115 165, 1992 and Fernig et al., Prog. Growth Factor Res. 5(4):353 377, 1994) that interact with the FGF tyrosine kinase recptors, and which generally act as mitogens for a broad spectrum of cell types. For example, basic FGF (also known as FGF-2) is mitogenic in vitro for endothelial cells, vascular smooth muscle cells, fibroblasts, and generally for cells of mesoderm or neuroectoderm origin, including cardiac and skeletal myocytes (Gospodarowicz et al., J. Cell. Biol. 70:395 405, 1976; Gospodarowicz et al., J. Cell. Biol. 89:568 578, 1981 and Kardami, J. Mol. Cell. Biochem. 92:124 134, 1990). In vivo, bFGF has been shown to play a role in avian cardiac development (Sugi et al., Dev. Biol. 168:567 574, 1995 and Mima et al., Proc. Nat'l. Acad. Sci. 92:467 471, 1995), and to induce coronary collateral development in dogs (Lazarous et al., Circulation 94:1074 1082, 1996). In addition, non-mitogenic activities have been demonstrated for various members of the FGF family. Non-proliferative activities associated with acidic and/or basic FGF include: increased endothelial release of tissue plasminogen activator, stimulation of extracellular matrix synthesis, chemotaxis for endothelial cells, induced expression of fetal contractile genes in cardiomyocytes (Parker et al., J. Clin. Invest. 85:507 514, 1990), and enhanced pituitary hormonal responsiveness (Baird et al., J. Cellular Physiol. 5:101 106, 1987)

FG-8 is a member of the FGF family that was originally isolated from mammary carcinoma cells as an androgen-inducible mitogen. It has been mapped to human chromosome 10q25-q26 (White et al., Genomics 30:109 11, 1995). FGF-8 is involved in growth and patterning of limbs (Vogel et al., Development 122:1737 1750, 1996; Yoshiura et al., Am. J. Med. Genet. 72: 354-362 and Tanaka et al., Current Biology 5(6):594 597, 1995) Expression of FGF8 during embryogenesis in cardiac, urogenital and neural tissue indicates that it may play a role in development of these tissues (Crossley et al., Development 121:439 451, 1995) There is some evidence that acrocephalosyndactylia, a congenital condition marked by peaked head and webbed fingers and toes, is associated with FGF8 point mutations (White et al., Genomics 30:109 11, 1995)

The complete function of FGF8 is still unknown; however, recent studies have linked FGF8 to a number of Quantitative Trait Loci affecting obesity in mice which indicates its potential for regulating adiposity in other species. In addition, Stylianou et al. (Mamm. Gen. 17, 22-36, 2006) suggests that FGF8 might act as a master regulator or interacting element controlling multiple genes that contribute to adiposity.

FGF8 has five exons, in contrast to the other known FGFs, which have only three exons. The first three exons of FGF-8 correspond to the first exon of the other FGFs (MacArthur et al., Development 121:3603 3613, 1995.) The human gene for FGF-8 codes for four isoforms which differ in their N-terminal regions: FGF isoforms a, b, e, and f; in contrast to the murine gene which gives rise to eight FGF-8 isoforms (Crossley et al., Development 121:439 451, 1995) Human FGF-8a and FGF-8b have 100% homology to the murine proteins, and FGF-8e and FGF-8f proteins are 98% homologous between human and mouse (Gemel et al., Genomics 35:253 257, 1996.)

Several studies have focused on the structure and function of human FGF8 (Gemel et al., Genomics 35: 253-257, 1996; Yoshiura et al. Am. J. Med. Genet. 72: 354-362, 1997) and mouse FGF8 (Crossley and Martin, Development, February 121(2); 439-451, 1995; Tanaka et al. PNAS USA 89; 8928-8932, 1992), but not much is known about it in other species. Human FGF8 maps to chromosome 10 and consists of 6 exons, with exons 2 and 3 encoding the C terminus showing 100% alignment with the corresponding mouse exons (Gemel et al., Genomics 35: 253-257, 1996). FGF8 androgen induced property was first discovered in earlier experiments by Tanaka et al. (PNAS USA 89; 8928-8932, 1992). This study reported that a mouse mammary carcinoma cell line was stimulated to secrete a number of FGFs when induced by androgens. These FGFs in turn demonstrated growth like properties on this carcinoma cell line. Isolation and characterization of the activity determined that FGF8 was contributing to some of the growth effects.

Polymorphisms in a candidate gene, such as FGF8, that show association with specific ERT may be useful quantitative trait nucleotides for marker-assisted selection. It remains advantageous to provide further SNPs, such as FGF8 SNPs, that may more accurately predict the meat quality phenotype of an animal and also a business method that provides for increased production efficiencies in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to the identification of single nucleotide polymorphisms (SNPs) within the bovine gene encoding fibroblast growth factor 8 ("FGF8") and their associations with economically relevant traits in beef production.

The invention encompasses a method for sub-grouping animals according to genotype wherein the animals of each sub-group have a similar polymorphism in a FGF8 gene which may comprise determining the genotype of each animal to be sub-grouped by determining the presence of a single nucleotide polymorphism in the FGF8 gene, and segregating individual animals into sub-groups wherein each animal in a sub-group has a similar polymorphism in the FGF8 gene.

The invention also encompasses a method for sub-grouping animals according to genotype wherein the animals of each sub-group have a similar genotype in the FGF8 gene which may comprise determining the genotype of each animal to be sub-grouped by determining the presence of a single nucleotide polymorphism(s) of interest in the FGF8 gene, and segregating individual animals into sub-groups depending on whether the animals have, or do not have, the single nucleotide polymorphism(s) of interest in the FGF8 gene.

The single nucleotide polymorphism(s) of interest may be selected from the group consisting of a C to A substitution at the 142892 nucleotide position in the exon of the FGF8 gene (SNP14), an C to T substitution at position 142864 in the exon of the FGF8 gene (SNP15), a G to C substitution at position 142606 in an intron of the FGF8 gene (SNP16) and a G to C substitution at position 139686 in the exon of the FGF8 gene (SNP 17).

The invention further relates to a method for sub-grouping animals according to genotype wherein the animals of each sub-group have a similar haplotype in the FGF8 gene which may comprise determining the genotype of each animal to be sub-grouped by determining the presence of any of the above SNPs, and segregating individual animals into sub-groups depending on whether the animals have, or do not have, any of the above SNPs in the FGF8 gene.

The invention also relates to method for identifying an animal having a desirable phenotype as compared to the general population of animals of that species, which may comprise determining the presence of single nucleotide polymorphisms in the FGF8 gene of the animal, wherein the presence of the SNP's are indicative of a desirable phenotype.

In an advantageous embodiment, the animal may be a bovine. In another advantageous embodiment, the FGF8 gene may be a bovine FGF8 gene.

The invention also encompasses computer-assisted methods and systems for improving the production efficiency for livestock having marketable tender meat using multiple data, and in particular the genotype of the animals as it relates to FGF8 SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within the FGF8 gene related to meat quality traits of the breed of animal and associating those data with other data about the animal or its herd, and maintaining those data in ways that are accessible. Another aspect of the invention encompasses a computer-assisted method for predicting which livestock animals possess a biological difference in meat quality, and which may include the steps of using a computer system, e.g., a programmed computer comprising a processor, a data storage system, an input device and an output device, the steps of: (a) inputting into the programmed computer through the input device data that includes a genotype of an animal as it relates to any one of the FGF8 SNPs described herein, (b) correlating meat quality predicted by the FGF8 genotype using the processor and the data storage system and (c) outputting to the output device the meat quality correlated to the FGF8 genotype, thereby predicting which livestock animals possess a particular meat quality.

Yet another aspect of the invention relates to a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic intake, growth or carcass merit in beef cattle and the genotype is a FGF8 genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which:

FIG. 1 depicts the nucleic acid sequence of the FGF8 locus on BTA26 (SEQ ID NO: 1). This corresponds to GenBank Accession # NW-930497.1

FIG. 2A depicts the nucleic acid sequence of BTA26, SNP14 and SNP15, reverse sequence (SEQ ID NO: 2)

FIG. 2B depicts the nucleic acid sequence containing the FGF8 SNP14, forward sequence (SEQ ID NO: 3)

FIG. 2C depicts the nucleic acid containing the FGF8 SNP15, forward sequence (SEQ ID NO 4)

FIG. 3A depicts the nucleic acid sequence containing the FGF8 SNP16 reverse sequence (SEQ ID NO: 5)

FIG. 3B depicts the nucleic acid sequence of the FGF8 SNP16 forward sequence (SEQ ID NO 6)

FIG. 4A depicts the nucleic acid sequence containing the FGF8 SNP17, reverse sequence (SEQ ID NO 7)

FIG. 4B depicts the nucleic acid sequence containing the FGF8 SNP17, forward sequence (SEQ ID NO 8)

DETAILED DESCRIPTION

Figure 5:
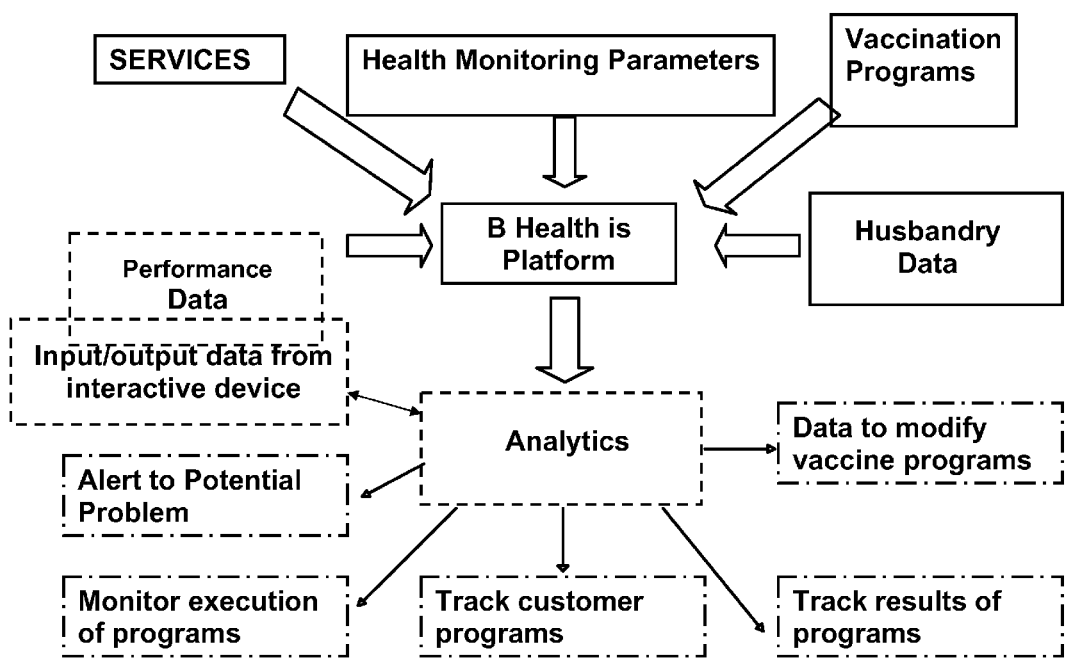
FIG. 5 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches.

The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine FGF8, the bovine FGF8 nucleotide sequence can be selected from, but is not limited to, the sequence corresponding to SEQ ID NO 1 (GenBank Accession No. NW_930497.1) or a fragment thereof or a region of the bovine genome that comprises this sequence.]

The present invention, therefore, provides isolated nucleic acids that may specifically hybridize to the nucleotide sequence corresponding to SEQ ID NO 1 (GenBank Accession No. NW_930497.1) or the complement thereof, and which comprises the polymorphic sites corresponding to nucleotides defined by SEQ ID NO 2 through 8.

The single nucleotide polymorphism(s) of interest may be selected from the group consisting of a C to A substitution at the 142892 nucleotide position in the exon of the FGF8 gene, an C to T substitution at position 142864 in the exon of the FGF8 gene, a G to C substitution at position 142606 in the intron of FGF8, and a G to C substitution at position 139686 in the exon of the FGF8 gene.

The SNPs advantageous in the present invention are associated with certain economically valuable and heritable traits relating to meat quality in bovines. Therefore, it is an object of the present invention to determine the genotype of a given animal of interest as defined by the FGF8 locus SNPs according to the present invention. It is also contemplated that the genotype of the animal(s) may be defined by additional SNPs within the FGF8 gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly with SNPs located within the FGF8 gene. The methods further allow, by computer-assisted methods of the invention, to correlate SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the FGF8 gene, advantageously of the region encompassing a FGF8 SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with a FGF8 gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in a FGF8 gene which are unique to a FGF8 gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3$H, $^{125}$I, $^{35}$S, $^{14}$C, $^{32}$P, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horseradish peroxidase, alkaline phosphatase etc.) colorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol. Biol. 167: 153-70 and MacBeath et al. (2001) Methods Mol. Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for desirable alleles of the FGF8 gene polymorphic sites associated with economically relevant traits of growth, feed intake, efficiency and/or carcass merit, would lead to a breed, line, or population having higher numbers of offspring with economically relevant traits of growth, feed intake, efficiency and carcass merit. Thus, the FGF8 SNPs of the present invention can be used as a selection tool.

Desirable phenotypes include, but are not limited to, feed intake, growth rate, body weight, carcass merit and composition, and milk yield. Specific carcass traits with desirable phenotypes include, but are not limited to, additional carcass value (additional carc value, $), average daily gain (ADG, lb/d), backfat thickness (BFAT, m), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF %, %), marbling score (MBS, 10 to 99), marbling score divided by days on feed (MBS/DOF), quality grade, less than or equal to select versus greater than or equal to choice (QG, <Se vs, > Ch), ribeye area (REA, in$^2$), ribeye area per hundred weight HCW (REA/cwt HCW, in$^2$/100 lb hot carcass weight (HCW) and subcutaneous fat depth (SFD).

One aspect of the present invention provides for grouping animals and methods for managing livestock production comprising grouping livestock animals such as cattle according the genotype as defined by panels of SNPs, each panel comprising at least one SNP, one or more of which are in the FGF8 gene of the present invention. Other SNPs that may be included in panels of SNPs include, but not limited to, SNPs found in the calpastatin gene, GHR gene, TFAM gene, GHR gene, FABP4 gene, ghrelin gene, leptin gene, NPY gene, ob gene, UASMS1 gene, UASMS2 gene, UASMS3 gene and/or the UCP2 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, feed intake, carcass/meat quality and milk production. The present invention provides methods of screening livestock to determine those more likely to develop a desired body condition by identifying the presence or absence of one or more gene polymorphisms correlated with meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or subgrouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), bovine spongiform encephalopathy (BSE) diagnosis, brucellosis vaccination, FMD (foot and mouth disease) vaccination, BVD (bovine viral diarrhea) vaccination, Sure Health preconditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are FGF8 sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the FGF8 sequences described herein.

Another embodiment of the invention is an oligonucleotide that specifically hybridizes under high stringency conditions to any one of the polymorphic sites of the FGF8 gene, wherein the oligonucleotide is between about 18 nucleotides and about 50 nucleotides.

In another embodiment of the invention, the oligonucleotide comprises a central nucleotide specifically hybridizing with a FGF8 gene polymorphic site of the portion of the nucleic acid molecule.

Another aspect of the invention is a method of identifying a FGF8 polymorphism in a nucleic acid sample comprising isolating a nucleic acid molecule encoding FGF8 or a fragment thereof and determining the nucleotide at the polymorphic site.

Another aspect of the invention is a method of screening cattle to determine those bovines more likely to exhibit a biological difference in meat quality comprising the steps of obtaining a sample of genetic material from a bovine; and assaying for the presence of a genotype in the bovine which is associated with meat quality, the genotype characterized by a polymorphism in the fibroblast growth factor 8 gene.

In other embodiments of this aspect of the invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the FGF8 gene or a portion thereof that contains the polymorphism. In other embodiments of the invention, the amplification may include the step of selecting a forward and a reverse sequence primer capable of amplifying a region of the FGF8 gene.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising a FGF8 genotype of an animal, (b) correlating growth, feed intake, efficiency or carcass merit quality predicted by the FGF8 genotype using the processor and the data storage system and (c) outputting to the output device the meat quality correlated to the FGF8 genotype, thereby predicting which livestock animals possess a particular growth level, feed intake, efficiency or carcass merit quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

This Example provides DNA loci, genetic polymorphisms and significant associations with carcass merit in beef cattle for the bovine fibroblast growth factor 8 (FGF8) gene.

In beef cattle the measurement of traits such as body composition or product quality are difficult and sometimes expensive to measure. This is particularly so for traits associated with lipid metabolism such as back-fat and marbling score or other traits such as muscle proportions or predictors of growth. The measurements are also usually taken at a time (post slaughter), when the animal clearly has no potential for breeding and after all the production costs and other inputs have already been incurred. The technology enables a predictive test for a proportion of variation in fattening capacity and fat compartmentalization, feed intake, growth and musculature. The test may also have application in dairy cattle as a predictor of milk fat content or milk yield.

The technology differs from existing technology in that it defines unique polymorphisms in the fibroblast growth factor 8 specifically associated with differences in body fat distribution, growth rate and feed intake in beef cattle.

The polymorphisms in FGF8 gene affecting variation of carcass merit can be used as markers for predicting carcass quality in beef cattle before animals are introduced into the market. Breeders can make decisions about the meat quality of these animals based on the test results from these polymorphisms early on in the production scheme. Currently, producers rely on statistical models to predict the best animals to be used in breeding programs improving the genetics of the next generation of offsprings.

TABLE 1

Summary of FGF8 SNP alleles, GenBank Accession number, and nucleotide position.

| SNP NAME | SNP | Location | Type of Mutation | GenBank Accession No. and Complimentary Strand Base Position |
|---|---|---|---|---|
| FGF8 SNP14 | C/A | Exon | Silent (Glycine to Glycine) | NW_930497.1 - 142892 |
| FGF8 SNP15 | C/T | Exon | glutamic acid (E) to lysine (L) change | NW_930497.1 - 142864 |

TABLE 1-continued

Summary of FGF8 SNP alleles, GenBank Accession number, and nucleotide position.

| SNP NAME | SNP | Location | Type of Mutation | GenBank Accession No. and Complimentary Strand Base Position |
|---|---|---|---|---|
| FGF8 SNP16 | G/C | Intron | | NW_930497.1 - 142606 |
| FGF8 SNP17 | G/C | Exon | Glycine (G) to Arginine (R) change | NW_930497.1 - 139686 |

TABLE 2

Genotype and allele frequencies of FGF8 SNPs in an experimental line of beef cattle (Angus, Charolais, and hybrid bulls)

FGF8 SNP14

| Sire Breed | Animals | CC | CA | AA | C allele frequency |
|---|---|---|---|---|---|
| ANGUS | 205 | 161 | 43 | 1 | 0.89 |
| CHAROLAIS | 117 | 73 | 43 | 1 | 0.81 |
| HYBRID | 140 | 97 | 41 | 2 | 0.84 |
| TOTAL | 462 | 331 | 127 | 4 | 0.86 |

FGF8 SNP15

| Sire Breed | Animals | TT | TC | CC | T allele frequency |
|---|---|---|---|---|---|
| ANGUS | 205 | 120 | 74 | 11 | 0.77 |
| CHAROLAIS | 117 | 34 | 59 | 24 | 0.54 |
| HYBRID | 140 | 37 | 73 | 30 | 0.53 |
| TOTAL | 463 | 191 | 206 | 65 | 0.63 |

| Sire Breed | Animals | GG | GC | CC | C allele frequency |
|---|---|---|---|---|---|

FGF8 SNP16

| | | | | | |
|---|---|---|---|---|---|
| ANGUS | 205 | 12 | 68 | 125 | .78 |
| CHAROLAIS | 117 | 6 | 38 | 73 | .79 |
| HYBRID | 141 | 8 | 51 | 82 | .76 |
| TOTAL | 463 | 26 | 157 | 280 | .77 |

FGF8 SNP17

| | | | | | |
|---|---|---|---|---|---|
| ANGUS | 204 | 0 | 6 | 198 | 0.98 |
| CHAROLAIS | 117 | 0 | 2 | 115 | 0.99 |
| HYBRID | 141 | 0 | 2 | 139 | 0.99 |
| TOTAL | 462 | 0 | 10 | 452 | 0.99 |

TABLE 3

Effect of fibroblast growth factor 8 (FGF8) haplotypes on growth and carcass merit in beef

| Haplotype | SNPs[a] | Traits | Estimate | P-value |
|---|---|---|---|---|
| C-C H2_1 | SNP 14, 15 | Ultrasound Backfat. mm | 0.004 ± 0.002 | 0.032 |
| C-C H2_1 | SNP 14, 15 | Ultrasound LM area, cm$^2$ | 1.944 ± 0.884 | 0.028 |
| C-C H2_1 | SNP 14, 15 | Gradefat, mm | 1.978 ± 0.362 | 0.007 |
| C-C H2_1 | SNP 14, 15 | Quality Grade | −0.160 ± 0.074 | 0.032 |
| C-T H1_1 | SNP 14, 15 | Ultrasound Backfat. mm | −1.138 ± 0.368 | 0.002 |
| C-T H1_1 | SNP 14, 15 | Lean Meat Yield, % | 0.832 ± 0.336 | 0.014 |
| G-G H3_2 | SNP 16, 17 | Ultrasound Marbling | 0.136 ± 0.061 | 0.025 |
| G-G H3_2 | SNP 16, 17 | Gradefat, mm | 0.779 ± 0.320 | 0.015 |
| G-G H3_2 | SNP 16, 17 | Birth Weight. kg | −1.210 ± 0.472 | 0.011 |
| T-C H1_3 | SNP 15, 16 | Ultrasound Backfat. mm | −0.571 ± 0.266 | 0.034 |
| T-C H1_3 | SNP 15, 16 | Gradefat, mm | −1.090 ± 0.395 | 0.007 |
| T-C H1_3 | SNP 15, 16 | Lean Meat Yield, % | 0.923 ± 0.368 | 0.013 |
| T-C H1_3 | SNP 15, 16 | Birth Weight. kg | 1.366 ± 0.501 | 0.007 |
| T-G H2_3 | SNP 15, 16 | Gradefat, mm | −0.695 ± 0.338 | 0.041 |
| T-G H2_3 | SNP 15, 16 | Ultrasound Backfat. mm | −0.918 ± 0.338 | 0.007 |
| T-G H2_3 | SNP 15, 16 | Lean Meat Yield, % | 0.715 ± 0.309 | 0.021 |

[a]SNP information available in Table 1.

TABLE 4

Effect of fibroblast growth factor 8 (FGF8) genotypes on carcass merit of beef steers

| FGF8 SNP15 | TT | TC | CC | P-value[b] | Additive Effect | Dominance Effect | Allele Subs. Effect[a] |
|---|---|---|---|---|---|---|---|
| Carcass Lean Meat Yield, % | 58.55 ± 0.37 | 58.25 ± 0.35 | 56.65 ± 0.55 | 0.006 | 1.90 ± 0.61, P = 0.002 | −0.65 ± 0.38, P = 0.091 | −0.77, P = 0.0072 |
| Carcass Backfat, mm | 11.30 ± 0.37 | 11.89 ± 0.34 | 13.50 ± 0.57 | 0.004 | −2.20 ± 0.66, P = 0.001 | 0.51 ± 0.42, P = 0.230 | 0.9619, P = 0.0021 |
| Carcass Gradefat, mm | 9.92 ± 0.36 | 10.34 ± 0.34 | 11.89 ± 0.57 | 0.011 | −1.97 ± 0.66, P = 0.003 | 0.57 ± 0.42, P = 0.179 | 0.8301, P = 0.0070 |

TABLE 4-continued

Effect of fibroblast growth factor 8 (FGF8) genotypes on carcass merit of beef steers

| FGF8 SNP16 | GG | GC | CC | P-value[b] | Additive Effect | Dominance Effect | Allele Subs. Effect[a] |
|---|---|---|---|---|---|---|---|
| Ultrasound Backfat, mm | 3.92 ± 0.09 | 3.98 ± 0.05 | 4.00 ± 0.04 | 0.048 | 0.04 ± 0.27, P = 0.87 | 0.34 ± 0.16, P = 0.04 | −0.16, P = 0.02 |
| Carcass Gradefat, mm | 10.29 ± 0.79 | 9.70 ± 0.35 | 10.94 ± 0.29 | 0.033 | −0.64 ± 0.85, P = 0.45 | 0.91 ± 0.53, P = 0.09 | −0.62, P⁻0.01 |
| Carcass Lean Meat Yield | 58.05 ± 0.76 | 58.78 ± 0.37 | 57.70 ± 0.32 | 0.040 | 0.35 ± 0.79, P = 0.66 | −0.91 ± 0.48, P = 0.06 | 0.542, P = 0.012 |
| Birth Weight, kg | 44.7 ± 1.2 | 43.8 ± 0.7 | 42.5 ± 0.7 | 0.042 | 2.2 ± 1.1, P = 0.050 | −0.1 ± 0.7, P = 0.824 | 1.1790, P = 0.0122 |
| Carcass LM area, cm2 | 82.83 ± 1.64 | 85.69 ± 0.85 | 82.89 ± 0.73 | 0.006 | −0.06 ± 1.69, P = 0.970 | −2.83 ± 1.03, P = 0.006 | 1.41, P = 0.002 |

[a]Allele substitution effect estimated by regression of phenotype on genotype dummy variables. The effect represents the regression coefficient (equal to the absolute effect) of genotype.
[b]P value from overall F-test.

TABLE 5

Effect of different FGF 8 markers on different traits in feedlot cattle

| Trait | Marker | Estimate | Std Err | P-value |
|---|---|---|---|---|
| Days on Feed | FGF8SNP14 | 0.215 | 0.135 | 0.1098 |
| Days on Feed | FGF8SNP15 | 0.157 | 0.107 | 0.1441 |
| Carcass Value, $ | FGF8SNP15 | 0.355 | 0.205 | 0.0837 |
| Carcass Backfat, in | FGF8SNP16 | −0.010 | 0.007 | 0.1168 |
| Percent Choice (QG) | FGF8SNP16 | −0.039 | 0.022 | 0.0837 |
| Average daily gain, lb | FGF8SNP17 | −0.104 | 0.044 | 0.0189 |
| Carcass Backfat, in | FGF8SNP17 | 0.025 | 0.014 | 0.0832 |
| Live Weight, lb | FGF8SNP17 | −19.199 | 9.813 | 0.0506 |
| Yield Grade | FGF8SNP17 | 0.108 | 0.068 | 0.1100 |
| Percent choice (MBS) | FGF8SNP17 | 0.148 | 0.058 | 0.0116 |
| Dry matter intake, lb | FGF8SNP17 | −86.396 | 40.266 | 0.0321 |
| Hot carcass weight, lb | FGF8SNP17 | −13.007 | 6.561 | 0.0476 |
| Marbling | FGF8SNP17 | 20.569 | 10.243 | 0.0449 |
| Rib eye area, in sq | FGF8SNP17 | −0.310 | 0.159 | 0.0510 |

Example 2

FIG. 5 shows a flowchart of the input of data and the output of results from the analysis and correlation of the data pertaining to the breeding, veterinarian histories and performance requirements of a group of animals such as from bovines. The flowchart illustrated in FIG. 5 further indicate the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 6:
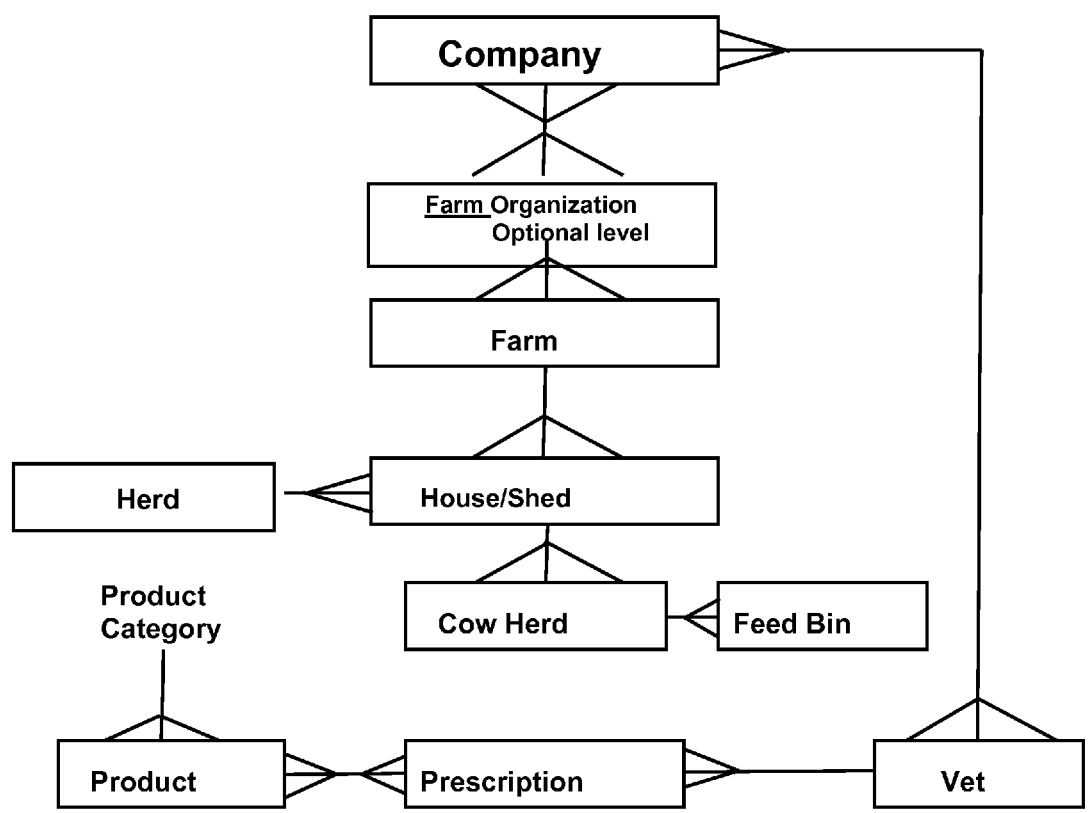
FIG. 6 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 6 illustrates potential relationships between the data elements to be entered into the system. Unidirectional arrows indicate, for example, that a house or shed is typically owned by only one farm, whereas a farm may own several houses or sheds. Similarly, a prescription may include have several veterinarian products.

Figure 7A:
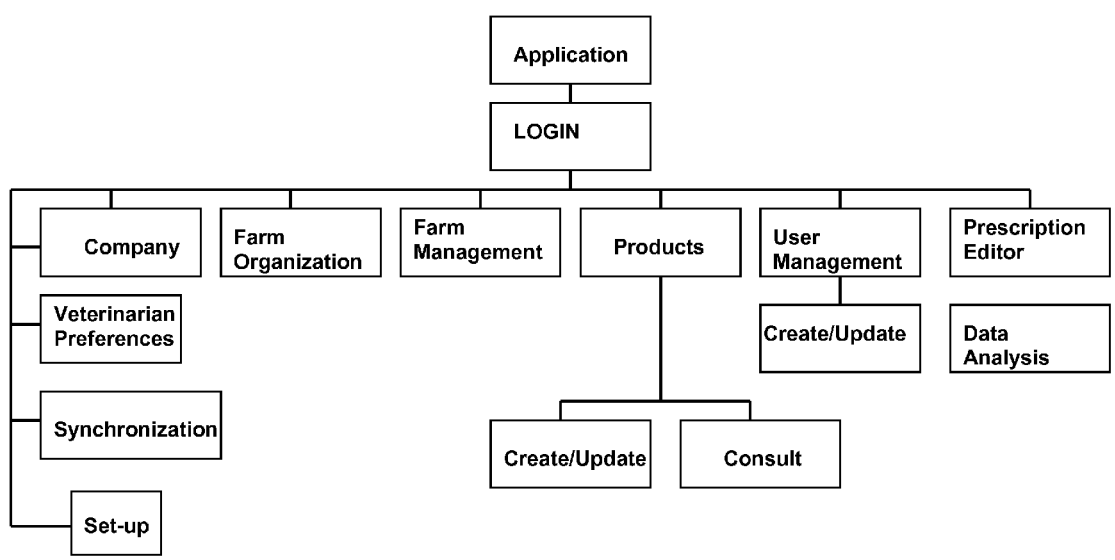
FIG. 7A illustrates the flow of events in the use of the portable computer-based system for data entry on the breeding and rearing of a herd of cows.
Figure 7B:
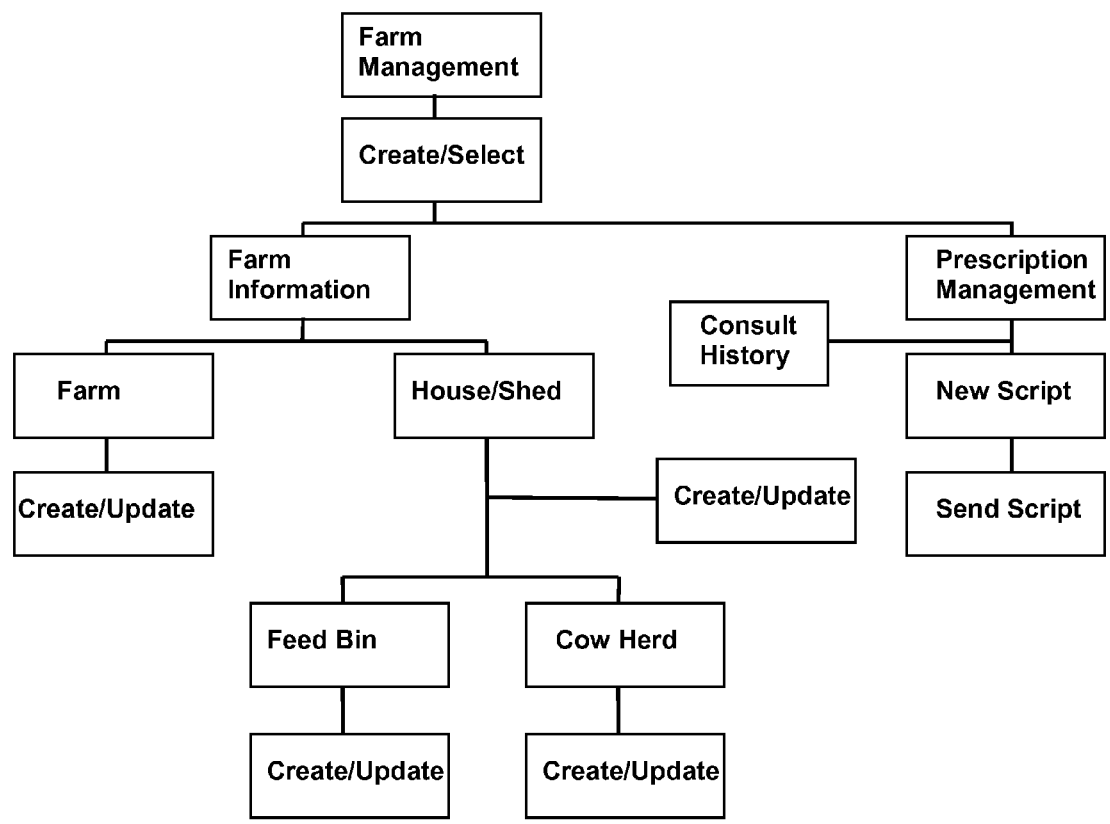
FIG. 7B illustrates the flow of events through the subroutines related to data entry concerning farm management.
Figure 7C:
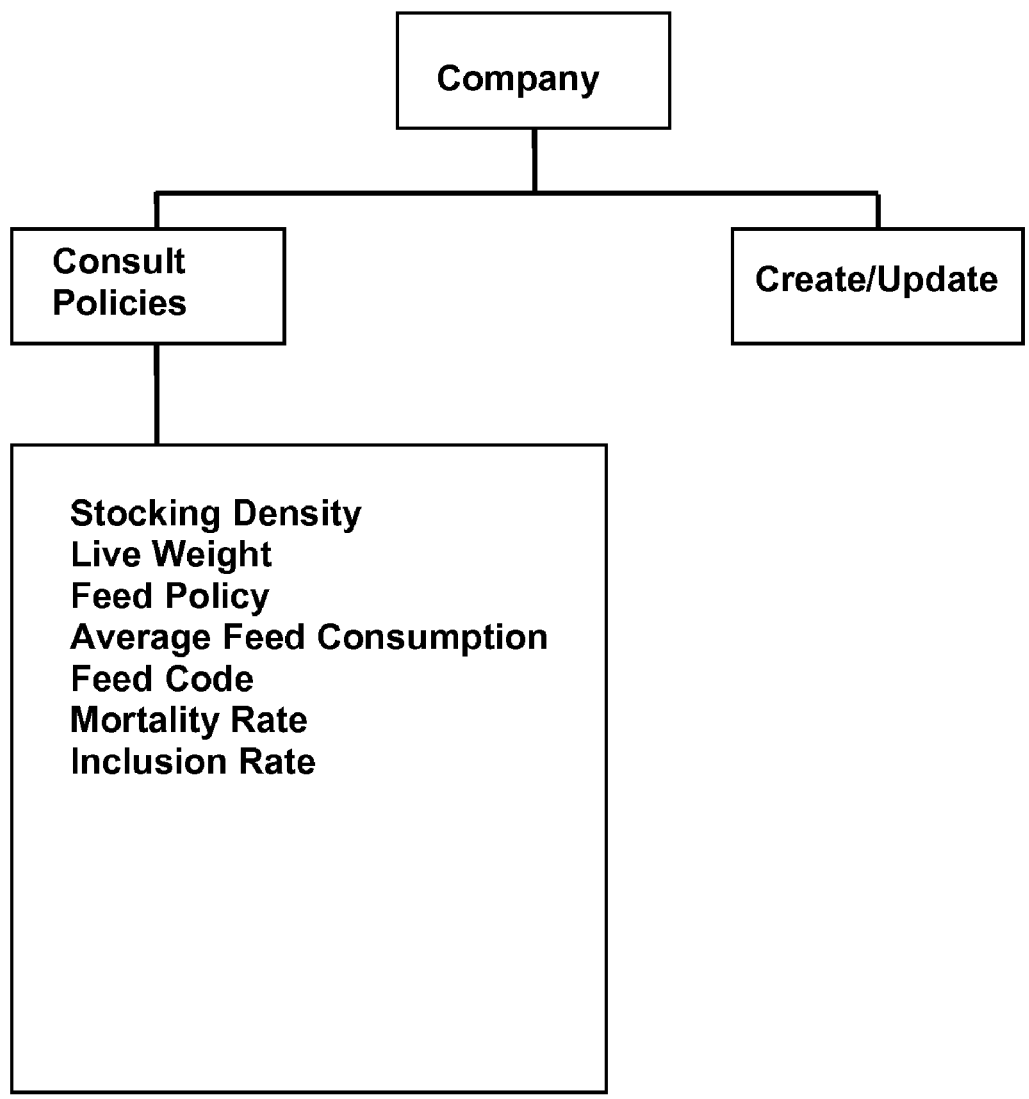
FIG. 7C illustrates the flow of events through the subroutines related to data entry concerning data specific to a company.

FIG. 7A illustrates the flow of events in the use of the portable computer-based system for data entry on the breeding and rearing of a herd of cows. FIG. 7B illustrates the flow of events through the sub-routines related to data entry concerning farm management. FIG. 7C illustrates the flow of events through the sub-routines related to data entry concerning data specific to a company.

Figure 8:
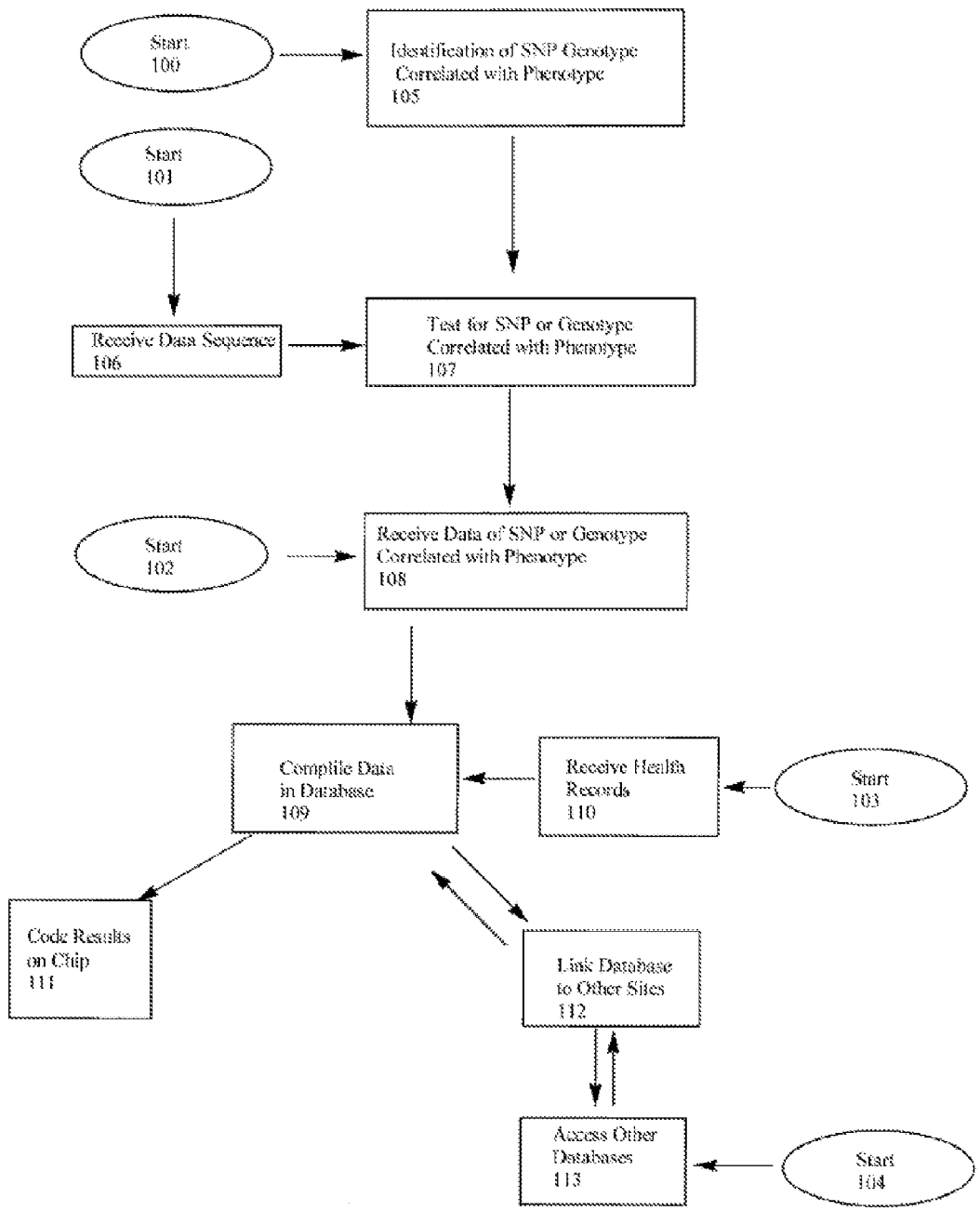
FIG. 8 illustrates a flow chart of the input of data and the output of results from the analysis and the correlation of the data pertaining to the breeding, veterinarian histories, and performance requirements of a group of animals.

FIG. 8 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have a similar polymorphism in a fibroblast growth factor 8 ("FGF8") gene comprising:

(a) determining the genotype of each animal to be sub-grouped by determining the presence of a single nucleotide polymorphism in the FGF8 gene, and (b) segregating individual animals into sub-groups wherein each animal in a sub-group has similar polymorphisms in the FGF8 gene.

2. A method for sub-grouping animals according to genotype wherein the animals of each sub-group have similar genotypes in the FGF8 gene comprising:

(a) determining the genotype of each animal to be sub-grouped by determining the presence of single nucleotide polymorphism(s) of interest in the FGF8 gene, (b) segregating individual animals into sub-groups depending on whether the animals have, or do not have, the single nucleotide polymorphism(s) of interest in the FGF8 gene.

3. The method of paragraphs 1 or 2, wherein the single nucleotide polymorphism(s) of interest is selected from the group, wherein the single nucleotide polymorphism(s) of interest is selected from the group consisting of a C to A substitution at the 142892 nucleotide position in the exon of the FGF8 gene, an C to T substitution at position 142864 in the exon of the FGF8 gene, a G to C substitution at position 142606 in the intron of FGF8, and a G to C substitution at position 139686 in the exon of the FGF8 gene.

4. A method for sub-grouping animals according to genotype wherein the animals of each sub-group have a similar genotype in the FGF8 gene comprising:

(a) determining the genotype of each animal to be sub-grouped by determining the presence of a C to A substitution at the 142892 nucleotide position in the exon of the FGF8 gene, an C to T substitution at position 142864 in the exon of the FGF8 gene, a G to C substitution at position 142606 in the intron of FGF8, and a G to C substitution at position 139686 in the exon of the FGF8 gene.

(b) segregating individual animals into sub-groups depending on whether the animals have, or do not have a C to A substitution at the 142892 nucleotide position in the exon of the FGF8 gene, an C to T substitution at position 142864 in the exon of the FGF8 gene, a G to C substitution at position 142606 in the intron of FGF8, and a G to C substitution at position 139686 in the exon of the FGF8 gene.

5. A method for identifying an animal having a desirable phenotype as compared to the general population of animals of that species, comprising determining the presence of a single nucleotide polymorphism(s) in the FGF8 gene of the animal, wherein the polymorphism is selected from the group consisting of a C to A substitution at the 142892 nucleotide position in the exon of the FGF8 gene, an C to T substitution at position 142864 in the exon of the FGF8 gene, a G to C substitution at position 142606 in the intron of FGF8, and a G to C substitution at position 139686 in the exon of the FGF8 gene.

6. The method of paragraph 5, wherein the desirable phenotype is feed intake, growth rate, body weight, carcass merit and composition, milk yield or any combination thereof.

7. The method of paragraph 5 or 6, wherein the desirable phenotype is birth weight (kg), gradefat (mm), lean meat yield (%), quality grade, ultrasound backfat (mm), ultrasound LM area (cm$^2$), ultrasound marbling or any combination thereof.

8. The method of any one of paragraphs 1 to 7 wherein the animal is a bovine.

9. The method of any one of paragraphs 1 to 8 wherein the FGF8 gene is a bovine FGF8 gene.

10. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

11. The method according to paragraph 10, wherein the computer system is an interactive system whereby modifications to the output of the computer-assisted method may be correlated according to the input from the interactive device.

12. The method according to paragraph 10 or 11, further comprising the steps of inputting into the programmed computer diagnostic data related to the health of the cow or herd of cows; and correlating the diagnostic data to the breeding and veterinary histories of the cow or herd of cows.

13. The method according to any one of paragraphs 10 to 12, wherein the veterinary data comprises a vaccination record for a cow or herd of cows.

14. The method according to any one of paragraphs 10 to 13 wherein the health data is selected from the group consisting of husbandry condition data, herd history, and food safety data.

15. The method according to any one of paragraphs 10 to 14, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

16. The method according to any one of paragraphs 10 to 15, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

17. The computer-assisted method according to any one of paragraphs 10 to 16 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

18. A method of transmitting data comprising transmission of information from such methods according to any one of paragraphs 10 to 16, selected from the group consisting of telecommunication, telephone, video conference, mass communication, a presentation, a computer presentation, a POWERPOINT™ presentation, internet, email, and documentary communication.

19. An interactive computer system according to any one of paragraphs 10 to 16 for tracking breeding and welfare histories of cows comprising breeding and veterinarian data corresponding to a bovine or herd of bovines, and wherein the computer system is configured to allow the operator thereof to exchange data with the device or a remote database.

20. The interactive computer system according to paragraph 19, wherein the input and output devices are a personal digital assistant or a pocket computer.

21. A method of doing business for tracking breeding and welfare histories of livestock comprising breeding and veterinarian data corresponding to one or more livestock animals comprising providing to a user the computer system of paragraph 19.

22. A method of doing business for tracking breeding and welfare histories of livestock comprising breeding and veterinarian data corresponding to one or more livestock animals comprising providing to a user the computer system of paragraph 20.

23. The method of doing business according to paragraph 21, further comprising providing the animal owner or customer with sample collection equipment, such as swabs and tags useful for collecting samples from which genetic data may be obtained, and wherein the tags are optionally packaged in a container which is encoded with identifying indicia.

24. The method of doing business according any one of paragraphs 10 to 16, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

25. The method of any one of paragraphs 8 to 24 wherein the data comprises presence or absence of one or more of a single nucleotide polymorphism(s) of interest in the FGF8 gene.

26. The method of paragraph, wherein the single nucleotide polymorphism(s) of interest is selected from the group consisting of a C to A substitution at the 142892 nucleotide position in the exon of the FGF8 gene, an C to T substitution at position 142864 in the exon of the FGF8 gene, a G to C substitution at position 142606 in the intron of FGF8, and a G to C substitution at position 139686 in the exon of the FGF8 gene.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal having a higher ultrasound backfat (UB), a higher ultrasound LM area (ULM), a higher gradefat, and a lower quality grade (QG), as compared to the general population of bovine animals, comprising the steps of:

(a) obtaining a biological sample from said bovine animal, wherein the sample contains a quantity of nucleic acids sufficient to enable genotyping analysis of a bovine fibroblast growth factor 8 ("FGF8") gene;

(b) detecting in said nucleic acids the presence of two single nucleotide polymorphisms (SNPs), which together comprise a haplotype (HAP), wherein the HAP comprises a C at positions corresponding to position 92 of SEQ ID NO:3 and position 64 of SEQ ID NO:4, in the same allele; and (c) correlating the presence of the nucleic acid content of (b) with higher UB, higher ULM, higher gradefat, and lower QG, thereby identifying said bovine animal.

2. A method for identifying a bovine animal having a lower ultrasound backfat (UB) and a higher lean meat yield % (LMY), as compared to the general population of bovine animals, comprising the steps of:

(a) obtaining a biological sample from said bovine animal, wherein the sample contains a quantity of nucleic acids sufficient to enable genotyping analysis of a bovine FGF8 gene;

(b) detecting in said nucleic acids the presence of two single nucleotide polymorphisms (SNPs), which together comprise a haplotype (HAP), wherein the HAP comprises a C at position corresponding to position 92 of SEQ ID NO:3 and a T at position 64 of SEQ ID NO:4, in the same allele; and (c) correlating the presence of the nucleic acid content of (b) with lower UB and higher LMY, thereby identifying said bovine animal.

3. The method of claim 1 or 2 further comprising sub-grouping animals according to genotype, wherein the animals of each sub-group have the same FGF8 gene HAP, said method comprising:

(a) determining the genotype of each animal to be sub-grouped by determining the presence of the HAP in the FGF8 gene, and (b) segregating individual animals into sub-groups depending on whether the animals have, or do not have, the FGF8 gene HAP.

* * * * *

```
                           SEQUENCE LISTING

<160> NUMBER OF SEQ ID NOS: 8

<210> SEQ ID NO 1
<211> LENGTH: 9790
<212> TYPE: DNA
<213> ORGANISM: Bos taurus
<220> FEATURE:
<221> NAME/KEY: modified_base
<222> LOCATION: (2192)..(2241)
<223> OTHER INFORMATION: a, c, g, t, unknown or other
<220> FEATURE:
<221> NAME/KEY: modified_base
<222> LOCATION: (4449)..(4635)
<223> OTHER INFORMATION: a, c, g, t, unknown or other
<220> FEATURE:
<221> NAME/KEY: modified_base
<222> LOCATION: (7106)..(7322)
<223> OTHER INFORMATION: a, c, g, t, unknown or other

<400> SEQUENCE: 1
atgtgcatcc ctggccccat gaaggggggct caggccccaa gaggacctgt gaggggtaag      60
gtagaggcca atctttgctc ctcctaccag tcatgcaggc catctctgag ccagcctgga     120
cccttagaaa cctgattcca ggggccagat ggaggggggct ggccagattg ggtgacaggg     180
aaaccagaat ccgggtggcc tggcatatgg gggcagagag gagccctgg gattcagcct      240 cctgggctaa agggttccag cccctagcc ctccacctgg tctggggatg gggggcggac      300
cgttctctgg tgcctgaaat caggtggttc tggggattgg ctgctgctgt accaggaaga     360
gaaagggatg tacctagtgt gagcatgagt gtgtatatga ccaagtctga ggtcagtagt     420
tcagcagctg tgttgatggg gcaggggggtc tcagtgccct acaaacaaac aaacaaaagg     480
ttacctcctg agacagcctg gggccagaca tgctgaggag ggacacagaa gagtgcctgg     540
tggggccagg cccactccct cccacattgg cttctgggca aatgagtgaa caagtgggag     600
gggtccctgg ataaccagaa gaggttggca ttggagcagg tgtttggaaa gagtgtttcc     660
acaacacaga aaagcactcc cttttcaaca catctccgaa ggaggtgccc ttctccctat     720
ggtgaggagc aaacaggtcc agggtttaac ctcccctttt cctagttgag gataaaggaa     780
gatgatccct ctctgcgtcg cagtgatcag ggtcgcaggc ctctctcttt gctgcaggac     840
tttcctgaag tgcttccacc aagaacactg ggatggagag ggcagccagg atgggaccat     900
tcaccaaccg caggcaaggg gtcaggagac agaggagaag gtggagttgg cgccctctgg     960
tgggcgaggt tgaaaccgct tgtggctgtg cagcttccca cgccgcctct gtagcggctc    1020
aaggccggcg ccgcggtgca ggggcctaca tgtcccgcca gccgtctgcg cgactaaggc    1080
agacttcatt cgttggttcg ttcattcatt cactggaagg gttcctgtta gaaccccttcc   1140 cttcctcctc tcgtctatcg cctccaaagt cctcggcacg tgttcggttg aaggcacggt    1200
agtctggctg agtgtaggga aaagttgggg aatccttccc agccgacact tctaccccccc   1260
```

-continued

```
gcaagtagcc ccgccccaat atttaccctc ctcgacgccg ctgatcgctc attgtgagcc      1320
cttctagttt cttggcgggt ctgcccgcgg ccctggccgg cgccaagcgc gctcctaccc      1380
gcggtggggg cccaatccac atccgcctcg tcccggagtt tctcgacccg acagggcgcc      1440
cacggactga gccgggaatt gttttttctc cctcccctcc ctcgtctctc ctcgatcccc      1500
ctttctgccc tctcagcgca cagtaggagc gttgcccatt catttcggtc tctgagccct      1560
gagggcttac gccgcggttt gcagactgct ggaggagggg caagactgta tttgggggtc      1620 gaaggggggac gaccagacgg ggcctagagt gcttaacaca gtctctgcga tttacatttg     1680
aacagtcggc ggagggtctg cggcgctttg aacgcctggt gcaggctgcg cgtgttggag      1740
cgcaggcggc ccccgccggt tggtgtggat ttgaggggcc cagggtgggc cagggggcggt    1800 gggagtgggc gaccgatgcg tttgaaaaga ggctgagcgt gtgtgtttgg gcccttgcaa      1860
cggtgtattt gcagagaggg gctatttgtg ttggcgagag gtgtgtgttt gtgtttgcag      1920
gaggcgagtg actctgtgtg tgtgtatttg tgtttgagga gtgtggggac ggccgggaaa     1980
ggtggccggg ctgtcactca gcgatcaggt tgacaggcgc tccctcatca gggccaggga     2040
gctctgattg cagattcgag gaaacaaaat agcaattgta attacggggc tttgataaga     2100
taaaggaagg agcaagccgg ccgggaggcg agtaagagca agggaggaga gaacggcctg     2160
ctggggcccc gatggagtat ttacatctgt cnnnnnnnnn nnnnnnnnnn nnnnnnnnnn     2220
nnnnnnnnnn nnnnnnnnnn ncacccccctc ccccatctag ggacagggac ttttggggat    2280
atgagaagaa tctcctcaaa tggacgaaga cccagttggg ggaagttctc aaaatgtaga     2340
ggaattctgg tctgtatagg ccccccgggggt agaggttagg gtgtgggact caaaccctga    2400
ttgatggtcc acacgtttag gccggggatg gcccatctct cggggagagt gaagagggtg     2460
gattaagatc attgaggttc agcccagcat cttcagaacc ttttgggggc tccaaaccag     2520
ggttgaactc tggtctgagc caggtgctat agtctccacc ccccactctg gggaaaggca     2580
ggtgcccaga gtgactcagg ttgtgactcc aggactacac acgctaagga tgggctggat     2640 gatgcccctga cccctgcttg ggtcctgctt cttgctgttc tcatcagact gttttcagag    2700
ggctggtccc tggtgagaag acccttttca tctgctgcct ctcatctctc cacttattta    2760
ttaatgcata caaataataa acatattcaa gggcctccta tgtgcagggc atgaggttaa     2820
gatggtgaat atttgcctg cttgaattag tgtacctggg gatgtagaca cccaacaact     2880
tctaagacag aggagctcaa atgaaggaga aatgctggtc taggcagtgg gtactggagc    2940
ccacttcact tgtcttcccc cagtgcccac ctcccagtgg ggttgagagg agatggtgca    3000
gacagccttt agcaaataca agtgctcaat aaatggtggt gcttatgatt cttatctgtt    3060
gggagggtgt tgaaggcaag gccccgcctg cactgaggtc taaatgctca gtcagtttcc    3120
ccattattca ttcattaaat acagaattgc agaaccctgc cctgctctcc tgagctagta    3180
agatgtggtc cttgcctgga ggtctgggtg ggaaagagcc acttgaggga acagactcaa    3240
gtgggtaaca ggtgagctca gggagtctgc ttctctgggg agggatgaga tcttgggaca    3300
agtctcctga ttctgttttcc ccatctagac cttgctcagt attagcacta tggctgggag    3360
tgggaaaggc aggccacaga gaaagggggaa gaacttggct gtgctgcctc tggtctcttg    3420
gtttcctgag gccatcccag cccctccagc ccaatcccca aggacatggg ggctggcagt    3480
agggcagggg aggtcttggg caagggcagc agctgggcaa agcatcagtg gctccacctg    3540
ctccccagaa ttttctgtct cagggcatct ctgcccaccc aagctgctct caaagaagca    3600
ccacacctcg cgggttcctg aagcccctgg aggaagcaat gggcggctgg gaaaggctta    3660
```

-continued

```
gacaactcac taccttcttt gatactttcc cctcccccag ggttgacaaa tcaccagtcc    3720
aagtttacca cacagtaggt gtgtaagtac ctgttcattg cacaaatagt gggactctga    3780
gcgaaaaaga ctaggcaacc tggatctaag tctctttccc aggaaaagca gctgaggtta    3840
ttttgcgccc actgcctgct gctttgggga gagcatggtg gtggcagtga ctggggtttt    3900
ccgtatgggt gggctctctc cttttttgggt ggtgtggtca ggcttcagtc tagcgtgttg   3960
ggggcgggag gtcgggggc ggacaggagc agggtgatg gtgataatga gagcaggaag      4020
caggaaagga gatgttcctc gatctcaggg ccttcttggt gactgaacga tgcaggagag   4080
accggcaagg cagggtactc agcaggaaga tgggagtggt tgtcggctcc cggtcgcaca   4140
ggcacgcact gccagaggaa agcgcacaac cgttcacccc agagttagag gctacttgca   4200
ggcggcagcc ccagacagac aaagcacaca gtaggtggct cagagaaccg ctgtctagct   4260
tgaggcttaa gcggaccggg tcccacggtg gagaccgggc gccttcccac tcgggcgccc   4320
ggggggtcca ggaagcccca gcagagggtc tcgggactcc acggggtggg cggcccgatg   4380
ggcccccatc cccgcgtgcc tggaccccaa gaacgcgcaa ggggacaagt ccgggatgcg   4440
gagaggcgnn nnnnnnnnnn nnnnnnnnnn nnnnnnnnnn nnnnnnnnnn nnnnnnnnnn   4500
nnnnnnnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnnnnnnnnn nnnnnnnnnn nnnnnnnnnn   4620
nnnnnnnnnn nnnnncagcc aggtgggggt ggttgggaa ctcggcgggc agccactccc    4680
ggccgcgccg aggaagggg cattcggagc caggggcat tcgatgtcag aggtccggtg     4740
actgcctcag ggaccccgctc cgcggctctt tggggagact tggcggcggg tctggccgaa  4800
agatcaggtg cccgggtctt ctgtggtctc aacatttgct ccgtgaattt gtctttataa   4860
atgtcagggg tcggccgct ctgcctcccg acttaaaagc gccctgctct tctaggaagg    4920
cccgggcggg gggcctgcgt tgggcaggga gctcgcttcc ctgttccgag ctggccggga   4980
gtcccagggt gtttcccaac aggtgggtcc agatccttcc ccatcccggg cgcatccata   5040
ctagactggg tctgtccgac ttccttgggt agggtggggg tggtccgaac tggcatgttg   5100
gggggacccc agccctgcc ggctgcctgg ggcagtggag ggaggtgccg ggtgatgggg    5160
gccactcggg cccctgggca gggtagcatt ataatgcgt gttgtgtatt tttcaatttc    5220
ctaaaggtaa ctgttcagtc ctcacctaat tttacacagc atgtgaggga gcagagcctg   5280
gtgacagatc agctcagccg ccgtctcatc cggacctacc aactctacag ccgcaccagc   5340
gggaagcacg tgcaggttct ggccaacaag cgcatcaacg ccatggcaga agacggggac   5400
cccttcggta aggagctaca ctgcactggg gttaaggtag tctgcggggc gcgcccctcc   5460
tccccaggct ggcctgctgt gacgggaccc agcagtcgcg tctgcgctga gctgaggcct   5520
gcaggctccc cagctcagaa gggaaggagt taagccgaca aagcatcttg ggggtcagct   5580
ggagaagaga gggctgggga agggaccctg ggagtactt ggcccatagg tgcccttttcc   5640
ctgcccagca gatgaatgaa gccaggaatc tccctttcca cctcccccct tcatacccct   5700
ccccactgca ggtggaggca gagggttcag ggggagggg cccaggttta agggaagctc    5760
ttgaaagagg atatgtcacc agggcccaca aaagcagagt gggaaagaga agggagagaa   5820
atcccctcaa ctctcccagg tttgggggc ggtgtactgc gaactttaaa tactttgatc    5880
aggagggtca attacacatg gggactaggc taggaaaggg gccttcccca cttcacttgt   5940
ccaggaaccc aggcggttgg tcagagcggg gctcctggct cccggtgggg tggtgagtac   6000
agggagctac tgtgggatgg agaggctgag gactgattga tttctaaaac attcaatatt   6060
```

```
cctgccttga aacaaggcca atttccagag tcctggatgt accaagagaa aagcaagtcc    6120
tctgggcggc tggtgttgtt tttagagagc gattattgtg agtttaaaaa cctttaaata    6180
atgaccaagt taaacaagca tgaaaggaga ggggaagact ctattaaaat gtaataaaaa    6240
ggtgaagcat tttaagagct aagaagaaaa atgaagaatg atataaaaca gaaaaagaac    6300
gagccttttt ttcagatgtg gagtttgaaa ggagttgcaa gtctgtaaat gttaaaaaag    6360
aggttcaaga ttgttctcta tgaatctctg gagagacccc cgcgtctggc agagcgatta    6420
aaactcttct tactttcacc ttttttaaca tttcctgaat actttctcct cttctcgagc    6480
cagtttgggg gatcgagtat gtctcgctgc attttttctg catcgacgta gctgacttcc    6540
cttcaaagct ggagaaggag acataatttt cctgggataa atctgtcact ggggtggaag    6600
aataggtttg aaaatgttaa gctttccaaa agcccggtcg ggaaagccgc tgtaaactgc    6660
cgccccagct ccccagctcc atccaggaag gagagtgggg gctttctgca gtggggtgg     6720 gggtggcctg cccggtggcc gagctcccct gctgggctgg cagggccagc ctgccgcccc    6780
tttgtccctt caaactggct gctcgttgcc cttctcagct tccaaggaaa gggaatgaat    6840
gcctggctcc tcctgggttt gctccattgg agcaaatggt ccagcatcct ccgggtttgg    6900
ggagcgaaga agacgctaag ctggtcatgg ggggattcat cttcagacat cagaagtctg    6960
atgcccactt ctcttcttac aattatatga ggcttcccag gttccctggt ccctgcctgg    7020
tgggcaggag caggagctgg agggcccaag agcagaggct tagggtgtat agccaggaca    7080
ggtagaatct ggggagaatg gcaaannnnn nnnnnnnnnn nnnnnnnnnn nnnnnnnnnn    7140
nnnnnnnnnn nnnnnnnnnn nnnnnnnnnn nnnnnnnnnn nnnnnnnnnn nnnnnnnnnn    7200
nnnnnnnnnn nnnnnnnnnn nnnnnnnnnn nnnnnnnnnn nnnnnnnnnn nnnnnnnnnn    7260
nnnnnnnnnn nnnnnnnnnn nnnnnnnnnn nnnnnnnnnn nnnnnnnnnn nnnnnnnnnn    7320
nntctatgct tctgcaaagg gaggcaggca gtcacaggct gggctgtgag gctgccttg     7380 ctgacctgtg cccatcacct cccattagtt tcagggtcag agaaggtgcc accttgtcag    7440
aataagctgg gaggtagccc tgggagtcac cagacttctt tgtcaaggag ggagaaggct    7500
gaaggaggga gggcaggaga cccagcccct ttggttccat cccaaacagc taagtcggtc    7560
ctcactctca aagggaggag ttgtacagag agtgggcagg ggccagggct tctgtggcaa    7620
gctggctgtc taagggaagg ggtaagaagg cacaggattc agctccctgt ctcctggctc    7680
ttgagtgaga ggcaagcaca catgattttc tcttctcctc ccctacagaa agtgtttgct    7740
cactggggta agaagcccag tgctgctaga ggggtgcaa gagaaaagac tattgaatta    7800
ctgacttctg aacactgggg ctggggtctg gagtgactgg gaagtatggg gaagagacag    7860
tatcctccta gctggtgtct gagtttctag gaaagcagcc agccatgggc tgtgtgtgga    7920
gggagagctg tcctcatccc tgtcaccttt gcagcagagc cggggtggag ggtggaagat    7980
gtggggtggg gtggagtggg ttggggtgga gggtgtcggg gggtggccaa ggctgtgggt    8040
tggaacccga ggtatcagaa gcaagagaga gtgctttat gtttgacctc aggagtggag    8100
gtcaccactg cacctggatg tttgtaataa cctgtgaggc acgtgcatat aatatttga    8160 actggaagaa tcctcataga tcttttgatt ggtagtggaa ttctagtcaa attaaatttt    8220
acttgaagcc tcaacacaaa aatcattgct gtctgattat aaaaaagggt cttcagtttg    8280
atggctctaa gaccctctg cataaaccag ttcagacacc atgatctcat ccattccccc    8340
tctgtaaacc caggctaggg gcctgaagcc cagaaagggg acttgacctt tccagggttg    8400
cacagcatat tagtggttgg agcccacagc ctgggcatct ggcccttgga gcagctgctt    8460
```

```
ctgggatggg ccagctgggg tagggacatg gagcactgga ggtcaggaag ctgccaataa      8520
ccacccccac cccaccccaa cctttcctga cagcaaagct catcgtggag acagacacct      8580
tcgggagccg ggttcgagta cgaggagctg agacaggcct ctacatctgc atgaacaaga      8640
agggaaaatt gattgccaag gtgaggtcct agaaagaagg gagggactgg ctagggcctg      8700
gggagcaggc tgggctggct gagctcctcc aggataccaa ctaagtgggc agagaggcag      8760
agggccacct tggggttacc taatgattgg gtgggggggtg gaggaggtga gggaggaggt      8820
aactgagaga tgaaaagcta taaaggcaaa ggaggaagaa ggaaggctag gaaggggct       8880
ggggagggggg tgtcggtaaa ttccatatat cttttttaaca aatcaccaaa ttgctttgct    8940
attatgtcca attacatggt accagcattt ggaatgttca gtaagccgag ggcccagccc      9000
ctcagccgag ctctgaaatg gccccattag tcacggctcc tctccagcct cgagctcccc      9060
gcttccctgg cttctggggc ccggggctca gcatctcctc accagccttc cctccccat       9120
agggtggtgg ccctggggct gcaggttagc gtcctgagat ggctgaggtg ggcaggtggg      9180
gaaacgggtg ctagcagctt gggccagact ggtgggcagg aggccagggt gggcaggggc      9240
tgggccccct ctctgcccct ctgtgttggg gcccagcccc tctgtagaca gccatgtgtc      9300
actgctaccc aggaggacag gaagttgccg ggtgggctgt gagttgtgag ggattagaga      9360
gcgggtgccc accctgccat ctgctggggt gcccacctgc tgtctggggc cgcctgccct      9420
ctgcctagga tgggagggggg ctccggacag agccgggtga caccgtgtct gccccccacc    9480
ctgcagagca acggcaaagg caaggactgc gtgttcacgg agatcgtgct ggagaacaat      9540
tacacggccc tgcagaacgc caagtacgag ggctggtaca tggcttttcac gcgcaaaggc     9600
cgaccccgca agggctccaa gacccggcag caccagcgcg aagtccactt catgaagcgg      9660
ctgccccgcg gccaccacac caccgagcag agcctgcgct tcgagttcct caactacccg      9720
cccttcacgc gcagcctgcg cggcagccag aggacttggg cccctgagcc ccgataggcc      9780
ctgccggccc                                                             9790

<210> SEQ ID NO 2
<211> LENGTH: 488
<212> TYPE: DNA
<213> ORGANISM: Bos taurus

<400> SEQUENCE: 2
gcgcacagta ggagcgttgc ccattcattt cggtctctga gccctgaggg cttacgccgc       60
ggtttgcaga ctgctggagg aggggcaaga ctgtatttgg gggkcgaagg gggacgacca      120
gacgggggcct aragtgctta acacagtctc tgcgatttac atttgaacag tcggcggagg    180
gtctgcggcg ctttgaacgc ctggtgcagg ctgcgcgtgt ggagcgcag gcggcccccg      240
ccggttggtg tggatttgag gggcccaggg tgggccaggg gcggtgggag tgggcgaccg      300
atgcgtttgg aaagaggctg agcgtgtgtg tttgggccct gcaacggtg tatttgcaga      360
gaggggctat ttgtgttggc gagaggtgtg tgtttgtgtt tgcaggaggc gagtgactct      420
gtgtgtgtgt atttgtgttt gaggagtgtg gggacggccg ggaaaggtgg ccgggctgtc      480
actcagcg                                                               488

<210> SEQ ID NO 3
<211> LENGTH: 180
<212> TYPE: DNA
<213> ORGANISM: Bos taurus

<400> SEQUENCE: 3
```

| | |
|---|---:|
| caaagcgccg cagaccctcc gccgactgtt caaatgtaaa tcgcagagac tgtgttaagc | 60 |
| actctaggcc ccgtctggtc gtccccctttc gmccccaaa tacagtcttg ccctcctcc | 120 |
| agcagtctgc aaaccgcggc gtaagccctc agggctcaga gaccgaaatg aatgggcaac | 180 |

```
<210> SEQ ID NO 4
<211> LENGTH: 179
<212> TYPE: DNA
<213> ORGANISM: Bos taurus

<400> SEQUENCE: 4
```

| | |
|---|---:|
| caaagcgccg cagaccctcc gccgactgtt caaatgtaaa tcgcagagac tgtgttaagc | 60 |
| actyaggccc cgtctggtcg tccccccttcg accccccaaat acagtcttgc ccctcctcca | 120 |
| gcagtctgca aaccgcggcg taagccctca gggctcagag accgaaatga atgggcaac | 179 |

```
<210> SEQ ID NO 5
<211> LENGTH: 526
<212> TYPE: DNA
<213> ORGANISM: Bos taurus

<400> SEQUENCE: 5
```

| | |
|---|---:|
| cgatccccctt tctgccctct cagcgcacag taggagcgtt gcccattcat ttcggtctct | 60 |
| gagccctgag ggcttacgcc gcggtttgca gactgctgga ggaggggcaa gactgtattt | 120 |
| gggggcgaa gggggacgac cagacggggc ctaaagtgct taacacagtc tctgcgattt | 180 |
| acatttgaac agtcggcgga gggtctgcgg cgctttgaac gcctggtgca ggctgcgcgt | 240 |
| gttggagcgc aggcggcccc cgccggttgg tgtggatttg aggggcccag ggtgggccag | 300 |
| gggcggtggg agtgggcgac cgatgcgttt ggaaagaggc tgagcgtgtg tgtttgggcc | 360 |
| cttgcaacgg tgtatttgca gagaggggct atttgtgttg gcgagaggtg tstgtttgtg | 420 |
| tttgcaggag gcgagtgact ctgtgtgtgt gtatttgtgt tggaggagtg tggggacggc | 480 |
| cgggaaaggt ggccgggctg tcactcagcg atcggggttg gacaga | 526 |

```
<210> SEQ ID NO 6
<211> LENGTH: 180
<212> TYPE: DNA
<213> ORGANISM: Bos taurus

<400> SEQUENCE: 6
```

| | |
|---|---:|
| caaatacaca cacacagagt cactcgcctc ctgcaaacac aaacacacac ctctcgccaa | 60 |
| caaatacaca cacacagagt cactcgcctc ctgcaaacac aaacasacac ctctcgccaa | 120 |
| cacaaatagc ccctctctgc aaatacaccg ttgcaagggc ccaaacacac acgctcagcc | 180 |

```
<210> SEQ ID NO 7
<211> LENGTH: 470
<212> TYPE: DNA
<213> ORGANISM: Bos taurus

<400> SEQUENCE: 7
```

| | |
|---|---:|
| ctgctcgcgg ctctttgggg agacttggcg gcgggtctgg ccgaaagatc aggtgcccgg | 60 |
| gtcttctgts gtctcaacat ttgctccgtg aatttgtctt tataaatgtc aggggtcggg | 120 |
| ccgtctgcc tcccgactta aaagcgccct gctcttctag gaaggcccgg gcggggggcc | 180 |
| tgcgttgggc agggagctcg cttccctgtt ccagctggc cgggagtccc aggtgtttc | 240 |
| ccaacaggtg ggtccagatc cttccccatc ccgggcgcat ccatactaga ctgggtctgt | 300 |
| ccgacttcct tgggtagggt ggatgagtcc tattttagtt tataaagctc ctttttttt | 360 |

```
ataggtttct agccggtttt tttttattt tttatttgtt tatttttttt tttttctttt      420 tttgttttt ttttttttt ttttttttgt tttttttttt tttttattt                   470

<210> SEQ ID NO 8
<211> LENGTH: 180
<212> TYPE: DNA
<213> ORGANISM: Bos taurus

<400> SEQUENCE: 8
cgggaggcag agcggcccga cccctgacat ttataaagac aaattcacgg agcaaatgtt       60
gagacsacag aagacccggg cacctgatct ttcggccaga cccgccgcca agtctcccca      120
aagagccgcg gagcgggtcc ctgaggcagt caccggacct ctgacatcga atgccccctg     180
```